United States Patent [19]

Hallinan et al.

[11] Patent Number: 5,576,315

[45] Date of Patent: Nov. 19, 1996

[54] SUBSTITUTED DIBENZOXAZEPINE COMPOUNDS AND METHODS FOR TREATING OSTEOPOROSIS AND ISCHEMIA

[75] Inventors: E. Ann Hallinan, Evanston; Timothy J. Hagen, Glenview; Robert K. Husa, Vernon Hills; Sofya Tsymbalov, Des Plaines, all of Ill.; Jean-Pierre Van Hoeck, Chastre, Belgium; Albert C. Lee, Fort Collins, Colo.

[73] Assignee: G.D. Searle & Co., Chicago, Ill.

[21] Appl. No.: 509,846

[22] Filed: Aug. 1, 1995

Related U.S. Application Data

[62] Division of Ser. No. 295,302, Aug. 24, 1994, Pat. No. 5,464,830, which is a continuation of Ser. No. 108,551, Aug. 24, 1993, Pat. No. 5,378,840, which is a continuation-in-part of Ser. No. 695,654, May 3, 1991, abandoned.

[51] Int. Cl.$^6$ ............... C07D 413/12; C07D 267/20; C07D 281/16; A61K 31/55
[52] U.S. Cl. ........................... 514/211; 540/547
[58] Field of Search ............... 540/547; 514/211

[56] References Cited

U.S. PATENT DOCUMENTS

| | | | |
|---|---|---|---|
| 3,534,019 | 10/1970 | Coyne et al. | 260/239 |
| 3,624,104 | 11/1971 | Cusik et al. | 260/333 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244.4 |
| 4,170,593 | 10/1979 | Mueller | 260/243.3 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,704,386 | 11/1987 | Mueller | 514/211 |
| 5,180,720 | 1/1993 | Husa et al. | 514/211 |
| 5,182,272 | 1/1993 | Hallinan et al. | 514/80 |
| 5,281,590 | 1/1994 | Husa et al. | 514/211 |
| 5,283,240 | 2/1994 | Hallinan et al. | 514/80 |

FOREIGN PATENT DOCUMENTS

| | | | |
|---|---|---|---|
| 0012385 | 6/1980 | European Pat. Off. | C07D 267/20 |
| 0193822 | 9/1986 | European Pat. Off. | C07D 267/20 |
| 0218077 | 4/1987 | European Pat. Off. | C07D 267/20 |
| 0512400 | 11/1992 | European Pat. Off. | C07D 413/12 |
| 6700603 | 7/1967 | Netherlands . | |
| 1170322 | 11/1969 | United Kingdom | C07D 87/54 |
| 1331892 | 9/1973 | United Kingdom | C07D 87/54 |
| 1522003 | 8/1978 | United Kingdom | C07D 267/20 |

OTHER PUBLICATIONS

Drower, et al. "The Antiociceptive Effects of Prostaglandin Antagonists in the Rat", *European Journal of Pharmacology*, 133, 249–256 (1987).

J. H. Sanner, et al. "Dibenzoxazepine Hydrazides as Prostaglandin Antagonists", *Intra–Science Chem. Rept.*, vol. 6, No. 1, 1–9 (1972).

K. Nagarajan, et al. "Synthesis of 10,11–Dihydrodibenz[b, f][1,4]oxazepine Derivatives as Potential Anticonvulsants & Psychotropic Agents", *Indian Journal of Chemistry*, vol. 24B, 840–844 (1985).

D. E. MacIntyre, et al. "Antagonism of Human Platelet Responses to Stimulatory and Inhibitory Prostaglandins", *Prog. Lipid. Res.*, 20(1–4) 453–9 (1981).

R. Gimet, et al. "Quantitative Determination of Polymorphic Forms in a Formulation Matrix Using the Near Infra–Red Reflectance Analysis Technique", *J. Pharmaceutical & Biomedical Analysis*, vol. 5, No. 3, 205–211 (1987).

J. H. Sanner, et al. "Structure–Activity Relationships of some Dibenzoxazepine Derivatives as Prostaglandin Antagonists", *Advances in the Biosciences*, 9, 139–148 (1972).

A. Rakovska, et al. "Antagonistic Effect of SC–19220 on the Responses of Guinea–Pig Gastric Muscles to Prostaglandins $E_1$, $E_2$, and $F_2$", *Arch. Int. Pharmacodyn.*, 268, 59–69 (1984).

W. E. Coyne, et al. "Anticonvulsant Semicarbazides", *J. Med. Chem.*, 11(6), 1158–1160 (1968).

K. Gyires, et al. "The Use of the Writhing Test in Mice for Screening Different Types of Analgesics", *Arch. Int. Pharmacodyn.*, 267, 131–140 (1984).

A. Bennett, et al. "Antagonism of Prostanoid–Induced Contractions of Rat Gastric Fundus Muscle by SC–19220, Soduim Meclofenamate, Indomethacin or Trimethoquinol", *Br. J. Pharmac.*, 71, 169–175 (1980).

C. A. Maggi, et al. "The Effect of SC–19220, a Prostaglandin Antagonist, on the Micturition Reflex in Rats", *European Journal of Pharmacology*, 152, 273–279 (1988).

(List continued on next page.)

*Primary Examiner*—Philip I. Datlow
*Attorney, Agent, or Firm*—Fitzpatrick, Cella, Harper & Scinto

[57] ABSTRACT

The present invention provides dibenzoxazepine compounds of Formula I:

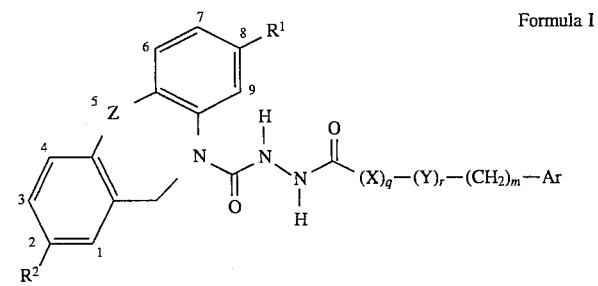

which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

4 Claims, No Drawings

OTHER PUBLICATIONS

George, et al. "Antagonism of Alcohol Hypnosis by Blockade of Prostaglandin Synthesis and Activity: Genotype and Time Course Effects", *Pharmacology Biochemistry & Behavior*, vol. 19, 131–136 (1983).

S. Nakajyo, et al. "Inhibitory Effect of Bassianolide, a Cyclodepsipeptide, on Drug–Induced Contractions of Isolates Smooth Muscle Preparations", *Japan. J. Pharmacol.*, 32, 55–64 (1982).

A. Gomes, et al. "Pharmacodynamics of Venom of the Centipede *Scolopendra subspinipes dehanni*", *Indian Journal of Experimental Biology*, vol. 20, 615–618 (1982).

SUBSTITUTED DIBENZOXAZEPINE COMPOUNDS AND METHODS FOR TREATING OSTEOPOROSIS AND ISCHEMIA

This application is a divisional application under 37 CFR §1.60 of application Ser. No. 08/295,302, filed on Aug. 24, 1994, now U.S. Pat. No. 5,464,830, which is a continuation application under 37 CFU §1.60 of application Ser. No. 08/108,551, filed on Aug. 24, 1993, now U.S. Pat. No. 5,378,840, which is a continuation-in-part application of Ser. No. 07/695,654, filed on May 3, 1991, now abandoned.

BACKGROUND OF THE INVENTION

1. Field of the Invention

The present invention generally relates to compounds having pharmacological activity which are useful as pharmacological agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

2. Description of the Related Art

U.S. Pat. No. 3,534,019 discloses hydrazides of dibenzoxazepine-, dibenzothiazepine- and dibenzodiazepinecarboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazine compounds.

U.S. Pat. Nos. 4,045,442, 4,125,532 (a divisional of U.S Pat. No. 4,045,442) and U.S. Pat. No. 4,170,593 (a divisional of U.S. Pat. No. 4,125,532) disclose 1-(substituted amino)alkanoyl-2-(dibenzoxazepine-10-carbonyl)hydrazine compounds.

U.S. Pat. Nos. 4,559,336 and 4,614,617 (a continuation-in-part of U.S. Pat. No. 4,559,336) disclose 8-chlorodibenz[b,f][1,4]-oxazepine-10(11H)-carboxylic acid, 2-(sulfinyl- and sulfonyl-containing acyl)hydrazides, and intermediates thereof.

U.S. Pat. No. 4,559,337 discloses 8-chlorodibenz[b,f][1,4]-oxazepine-10(11H)-carboxylic acid, 2-(alkoxy-containing acyl)hydrazide compounds.

GB 1 522 003 discloses 1-acyl-2-(8-chloro-10, 11-dihydrodibenz[b,f][1,4]oxazepine-10-carbonyl)hydrazine compounds.

GB 1 331 892 discloses derivatives of dibenzoxazepine N-carboxylic acid hydrazides.

European Patent Application Publication No. 0 193 822 discloses 8-chlorodibenz[b,f][1,4]-oxazepine-10(11H)-carboxylic acid, 2-(thio-, sulfinyl- and sulfonyl-containing acyl)hydrazide compounds.

European Patent Application Publication No. 0 218 077 discloses 8-chlorodibenz[b,f][1,4]oxazepine-10(11H)-carboxylic acid, 2-[(substituted phenylsulfinyl)alkanoyl]hydrazide compounds and 8-chlorodibenz[b,f][1,4]oxazepine-10(11H)-carboxylic acid, 2-[(substituted phenylsulfonyl)alkanoyl]hydrazide compounds, and intermediates used in the preparation of these compounds.

Drower et al., "The Antiociceptive Effects of Prostaglandin Antagonists in the Rat," European *Journal of Pharmacology*, 133, 249–256 (1987), disclose the study of the antinociceptive properties of two competitive antagonists of prostaglandins of the E series, 8-chlorodibenz[b,f][1,4]-oxazepine-10(11H)-carboxylic acid, 2-acetylhydrazide and 8-chlorodibenz[b,f][1,4]-oxazepine-10(11H)-carboxylic acid, 2-(5-chloro-1-oxopentyl)hydrazide.

J. H. Sanner, "Dibenzoxazepine Hydrazides as Prostaglandin Antagonists," *Intra-Science Chem. Rept.*, 6(1), 1–9 (1972), describes experiments performed with two dibenzoxazepine derivatives designated SC-18637 and SC-19220, and shown below, and found that SC-18637 and SC-19220 inhibit the stimulant actions of prostaglandins on isolated smooth muscle preparations.

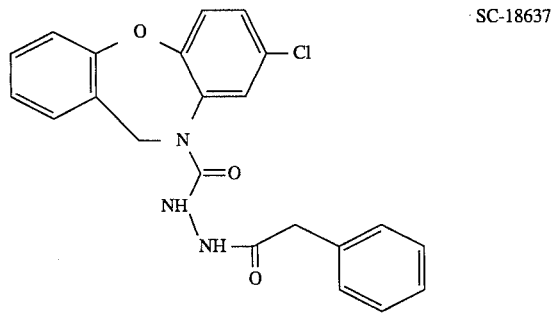

SC-18637

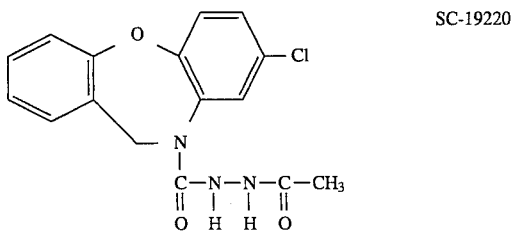

SC-19220

K. Nagarajan et al., "Synthesis of 10,11-Dihydrodibenz[b,f][1,4]oxazepine Derivatives as Potential Anticonvulsants & Psychotropic Agents," *Indian Journal of Chemistry*, 24B, 840–844 (1985), disclose the synthesis of acyl, carbamoyl and thiocarbamoyl derivatives of 10,11-dihydrodibenz[b,f]

[1,4]oxazepine, most of which have either a nitro or an amino group at position-2, as analogues of carbamazepine, and the evaluation of these derivatives as anticonvulsants associated with neuroleptic activity.

Other art which relates to the present invention includes that which is discussed below.

D. E. MacIntyre et al., "Antagonism of Human Platelet Responses to Stimulatory and Inhibitory Prostaglandins," *Prog. Lipid. Res.*, 20(1–4), 453–9 (1981), disclose on Page 454, Lines 11–12, Page 458, Lines 43–44, and in Table 1, two dibenzoxazepine compounds designated SC-19220 and SC-25191, and shown above and below, respectively, which were employed in an investigation of the effects of prostaglandin antagonists on platelet responses to stimulatory and inhibitory prostaglandins.

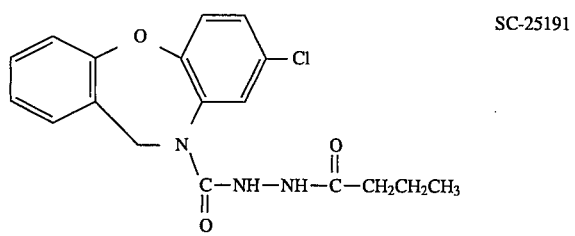

R. Gimet et al., "Quantitative Determination of Polymorphic Forms in a Formulation Matrix Using the Near Infra-Red Reflectance Analysis Technique," *J. Pharmaceutical & Biomedical Analysis*, 5(3), 205–211 (1987), disclose an analytical method for the determination of the polymorphic transformation of an active ingredient in a solid dosage form matrix, and discuss a compound designated SC-25469, and shown below, at Page 206, Lines 16–23.

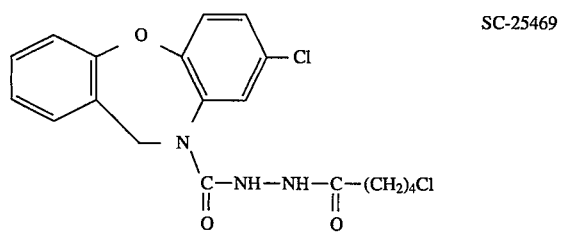

J. H. Sanner et al., "Structure-Activity Relationships of some Dibenzoxazepine Derivatives as Prostaglandin Antagonists," *Advances in the Biosciences*, 9, 139–148 (1972), disclose tests for prostaglandin antagonism on isolated guinea-pig ileum and rat stomach fundus strips with the n-butanoyl, i-butanoyl and n-hexanoyl analogs of SC-19220 (see structure above) and, on Page 140, Lines 11–18, show the chemical structures of the compounds used in the study.

A. Rakovska et al., "Antagonistic Effect of SC-19220 on the Responses of Guinea-Pig Gastric Muscles to Prostaglandins $E_1$, $E_2$ and $F_2$," *Arch. int. Pharmacodyn*, 268, 59–69 (1984), disclose a study of the contractile responses of guinea-pig gastric muscles to SC-19220 (see structure above), and the prostaglandin-blocking activity and specificity of SC-19220 on these muscles.

W. E. Coyne et al., "Anticonvulsant Semicarbazides," *J. Med. Chem.*, 11(6), 1158–1160 (1968), disclose the investigation of the structure-activity relationship of the anticonvulsant activity of a series of semicarbazides which was synthesized from various tricyclic amines (see Table I, Page 1160).

K. Gyires et al., "The Use of the Writhing Test in Mice for Screening Different Types of Analgesics," *Arch. int. Pharmacodyn*, 267, 131–140 (1984), describe a comparison of the analgesic potency of some prostaglandin synthesis inhibitors, including SC-19220 (see structure above), and morphine using the writhing test. SC-19220 is discussed on Page 133, Lines 10 and 14–16, in Table II (Page 134), and on Page 135, Lines 16–25, and Page 137, Lines 34–38.

A. Bennett et al., "Antagonism of Prostanoid-Induced Contractions of Rat Gastric Fundus Muscle by SC-19220, Sodium Meclofenamate, Indomethacin or Trimethoquinol," *Br. J. Pharmac*, 71, 169–175 (1980), disclose the study of the effects of several compounds, including SC-19220 (see structure above), on contractions of the rat stomach longitudinal muscle to several prostanoids. SC-19220 is discussed on Page 175, Paragraph 1, Page 170, Paragraph 4, in Table 1 and FIG. 2, on Page 172, Paragraph 2, and on Page 174, Paragraphs 1 and 2.

C. A. Maggi et al., "The Effect of SC-19220, a Prostaglandin Antagonist, on the Micturition Reflex in Rats," *European Journal of Pharmacology*, 152, 273–279 (1988), disclose a study in which SC-19220 (see structure above) is said to have increased the bladder capacity and reduced the voiding efficiency of micturition of urethane-anesthetized rats.

George et al., "Antagonism of Alcohol Hypnosis by Blockade of Prostaglandin Synthesis and Activity: Genotype and Time Course Effects," *Pharmacology Biochemistry & Behavior*, 19, 131–136 (1983), disclose a study of genetic and time-course factors of the effect of the antagonism of alcohol-induced behaviors of mice which have been pretreated with prostaglandin synthetase inhibitors and the effect of SC-19220 (see structure above) on ethanol sleep time.

S. Nakajyo et al., "Inhibitory Effect of Bassianolide, A Cyclodepsipeptide, on Drug-Induced Contractions of Isolates Smooth Muscle Preparations," *Japan. J. Pharmacol.*, 32, 55–64 (1982), disclose a study of the effect of bassianolide on the contractile responses induced by various types of neurotransmitters and autacoids. SC-19220 (see structure above) was employed in this study and is discussed on Page 57, Paragraph 1, in FIGS. 2 and 3, in Table 1, and on Page 60, Paragraph 1, Page 62, Paragraph 3, and Page 63, Paragraph 2.

A. Gomes et al., "Pharmacodynamics of Venom of the Centipede *Scolopendra subspinipes dehaani*," *Indian Journal of Experimental Biology*, 20, 615–618 (1982), disclose an investigation of the pharmacodynamic actions of the venom of the tropical centipede *S. subspinipes*. SC-19220 (see structure above) was employed in this study and is discussed on Page 615 (abstract), Page 616, Line 30, Page 617, Lines 13–18, in FIGS. 4 and 5, and on Page 618, Lines 23–26.

Each of the documents described hereinabove discloses compounds which are structurally different from the compounds of the present invention. Thus, the compounds of the present invention are structurally distinct from that which has been described in the art.

compounds of the present invention have been found to exhibit activity as prostaglandin $E_2$ antagonists. Compounds within the present invention were surprisingly and unexpectedly found to be more than eighty times more effective as prostaglandin $E_2$ antagonists than prostaglandin $E_2$ antagonists reported in the literature.

Moreover, compounds within the present invention were surprisingly and unexpectedly found to be water soluble. Thus, these compounds may be much more easily formulated into compositions which are suitable for oral, parenteral and other modes of administration than similar compounds which are not water soluble.

SUMMARY OF THE INVENTION

The present invention provides compounds having a structure of Formula I:

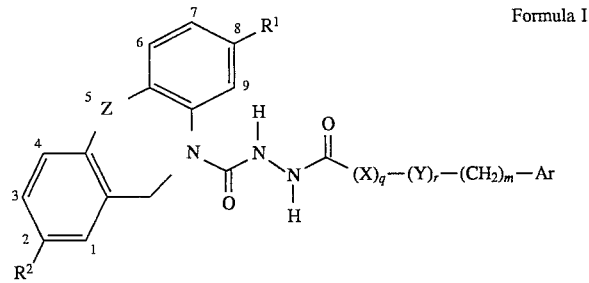

Formula I or a pharmaceutically-acceptable salt thereof, wherein:
$R^1$ is: hydrogen, halogen or —$CF_3$;
$R^2$ is: hydrogen, halogen, —OH or —$OCH_3$;
Z is: oxygen, sulfur,

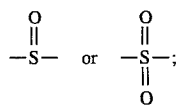

X is: —CH=CH—, —$CF_2$—, —CHF—, —$(CH_2)_n$— or —$(CH_2)_p$—CH=CH—;
Y is:

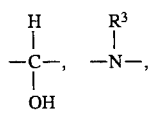

sulfur,

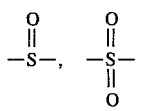

or oxygen;
q is: 0 or 1;
r is: 0 or 1, provided that r is not 0 when:
(1) X is —CH=CH—, —$(CH_2)_n$— or —$(CH_2)_p$—CH=CH—, q is 1 and Ar is imidazolyl or phenyl,
(2) X is —$(CH_2)_n$—, q is 1, n is 1 and Ar is phenyl substituted with halogen, methyl or alkoxy, or
(3) q is 0, m is 1, 2, 3, 4, 5 or 6, and Ar is imidazolyl or phenyl;
m is: an integer of from 0 to 6,
provided that m is not 0 when X is —$(CH_2)_n$—, q is 1, Y is oxygen, sulfur,

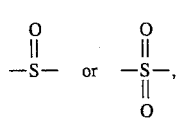

and Ar is phenyl;
n is: an integer of from 1 to 6;
p is: an integer of from 1 to 6;
$R^3$ is: hydrogen or t-butyloxycarbonyl; and
Ar is: aryl, alkyl-substituted aryl or aryl-substituted aryl.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviation "Ac" and the term "acetyl" as used herein mean the radical

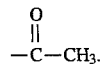

The abbreviation "Al" as used herein means aluminum.

The term "alkyl" as used herein means a saturated hydrocarbon radical having from one to ten carbon atoms, and within which includes from one to six carbon atoms, and further within which includes from one to three carbon atoms, which can be a straight or branched chain. Representative of such radicals are methyl, ethyl, n-propyl, isopropyl, n-butyl, sec-butyl, isobutyl, tert-butyl and the like.

The term "aryl" as used herein means 5- and 6-membered single-ring aromatic radicals which may include from zero to four heteroatoms. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The phrase "alkyl-substituted aryl" as used herein means an aryl radical, as defined above, having one or more hydrogen atoms replaced by an alkyl radical, as defined above, for example phenylethyl and N-methylpyrrolyl.

The phrase "aryl-substituted aryl" as used herein means an aryl radical, as defined above, having one or more hydrogen atoms replaced by an aryl radical, as defined above, for example thienyl-pyridinyl.

The term "analgesia" as used herein means the reduction, or absence, of sensibility to pain, designating particularly the relief of pain without loss of consciousness.

The term "animal" as used herein includes mammals and non-mammals, and further includes humans and non-human mammals.

The abbreviation "Boc" as used herein means t-buryloxycarbonyl.

The term "composition" as used herein means a product which results from the combining of more than one element or ingredient.

The abbreviation "DCM" as used herein means dichloromethane.

The phrase "$EC_{50}$ dose" as used herein means that dose of a compound or drug which is necessary to elicit a 50% maximal biological response and, thus, which is necessary to elicit a 50% reduction in the contractions of guinea pig ileum segments in a prostaglandin antagonism assay.

The phrase "$ED_{50}$ dose" as used herein means that dose of a compound or drug which produced a biological effect, such as producing analgesia, in 50% of the animals to which the compound or drug was administered.

The abbreviation "Et" as used herein means ethyl (—$CH_2CH_3$).

The abbreviation "EtOAc" as used herein means ethyl acetate.

The abbreviation "EtOH" as used herein means ethanol ($CH_3$—$CH_2$—OH).

The term "halo" or "halogen" as used herein means chlorine (Cl), bromine (Br), fluorine (F) and iodine (I).

The term "heteroatom" as used herein means an atom of any element other than carbon or hydrogen.

The abbreviation "HOAc" as used herein means acetic acid.

The abbreviation "i.g." as used herein means that a compound or drug was administered intragastrically, as defined below.

The term "intragastrically" as used herein means that a compound or drug was administered into the stomach.

The abbreviation "Me" as used herein means methyl (—$CH_3$).

The abbreviation "$^1$H NMR" as used herein means Proton Nuclear Magnetic Resonance.

The abbreviation "Pd" as used herein means palladium.

The abbreviation "Ph" as used herein means phenyl, as defined below.

The term "phenyl" as used herein means the group $C_6H_5$—, derived from benzene.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal ingection and infusion.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" as used herein refers to non-toxic salts of the compounds of the present invention which are generally prepared by reacting the free base with a suitable organic or inorganic acid or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts and alkali metal salts such as sodium and potassium and alkaline earth salts, such as calcium and magnesium.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "s.c." as used herein means subcutaneously.

The abbreviation "t-Bu" as used herein means tert-butyl.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "Zn" as used herein means zinc.

(2) Description of Invention

In one aspect, the present invention provides compounds comprising a structure of Formula I, as described above, and pharmaceutically-acceptable salts thereof.

The compounds of the present invention comprise a class of substituted dibenzoxazepine compounds in which the 2-, 5- and/or 8-position, and/or the side chain, is substituted. Such compounds have been shown to exhibit activity as prostaglandin $E_2$ antagonists.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmirate, stearate, laurate, benzoate, lactate, phosphate, rosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66, 1–19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal comprising administering a therapeutically-effective amount of a compound of Formula I, as described hereinabove, to the animal.

The most preferred embodiments of this invention are the compounds described in Examples 11, 13 and 44 below.

(3) Utility

Compounds of the present invention exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I.

While General Reaction Schemes Nos. 1–4 illustrate methods for attaching Ar—$(CH_2)_m$—$(Y)_r$—$(X)_q$—COOH, or derivatives thereof, to the dibenzoxazepine ring system, General Reaction Schemes Nos. 5–11 illustrate methods for synthesizing Ar—$(CH_2)_m$—$(Y)_r$—$(X)_q$—COOH. General Reaction Schemes Nos. 12–14 illustrate the synthesis of compounds of the present invention which are not encompassed in General Reaction Schemes Nos. 1–4.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

GENERAL REACTION SCHEME NO. 1

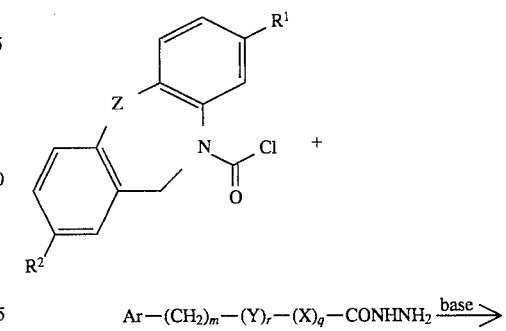

Ar—$(CH_2)_m$—$(Y)_r$—$(X)_q$—CONHNH$_2$ $\xrightarrow{\text{base}}$

GENERAL REACTION SCHEME NO. 1
-continued
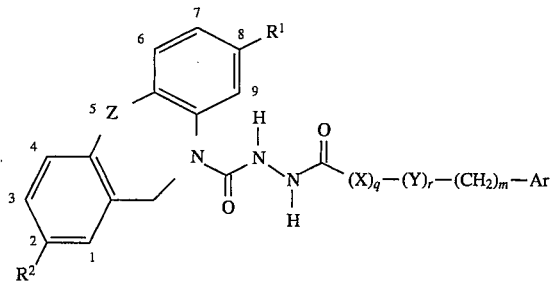
GENERAL REACTION SCHEME NO. 3
-continued
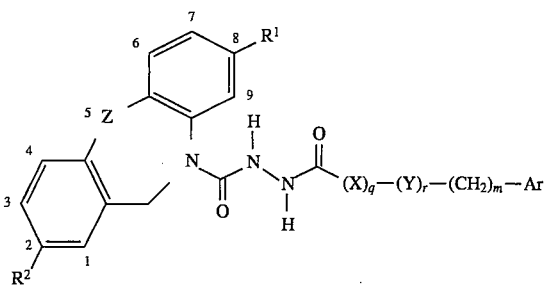
GENERAL REACTION SCHEME NO. 2
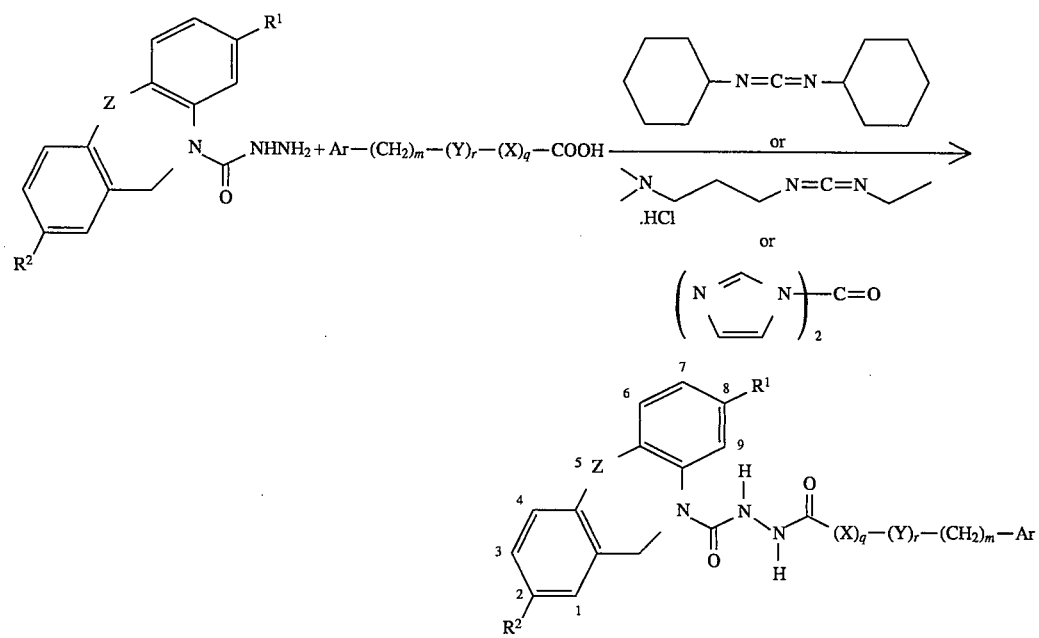
GENERAL REACTION SCHEME NO. 3
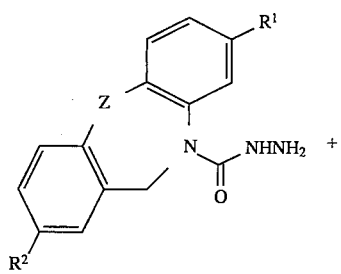
GENERAL REACTION SCHEME NO. 4
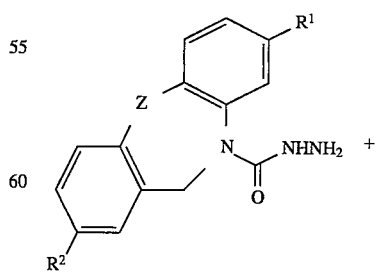

GENERAL REACTION SCHEME NO. 4
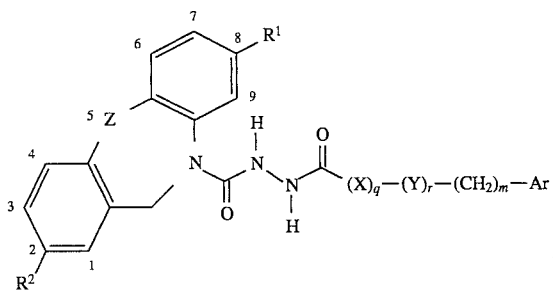
GENERAL REACTION SCHEME NO. 5
ArCHO + Ph₃P=CHCOOEt ⟶
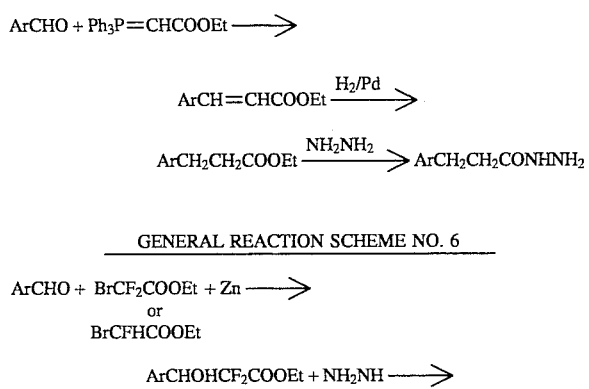
GENERAL REACTION SCHEME NO. 6
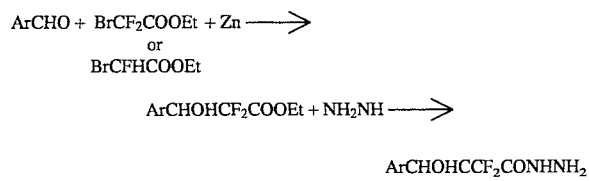
GENERAL REACTION SCHEME NO. 7
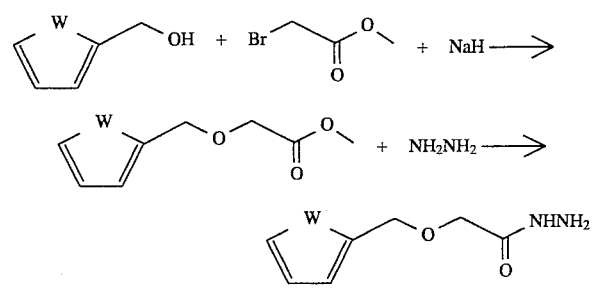
where W=O or S or NH or NMe
GENERAL REACTION SCHEME NO. 8
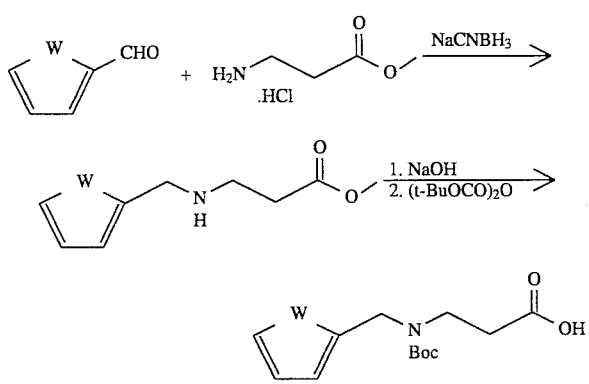
where W=O or S or NH or NMe
GENERAL REACTION SCHEME NO. 9
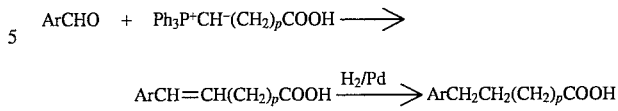
GENERAL REACTION SCHEME NO. 10
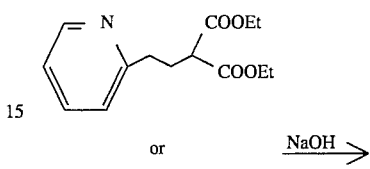
V. Boekeiheide and S. Rothchild,
J. Amer. Chem. Soc., (1949), 71, 879
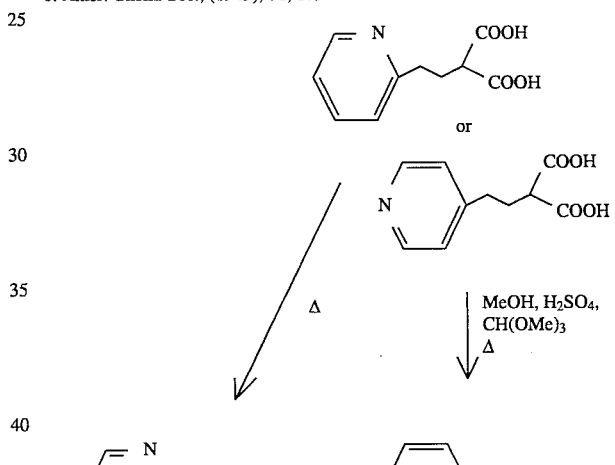
GENERAL REACTION SCHEME NO. 11
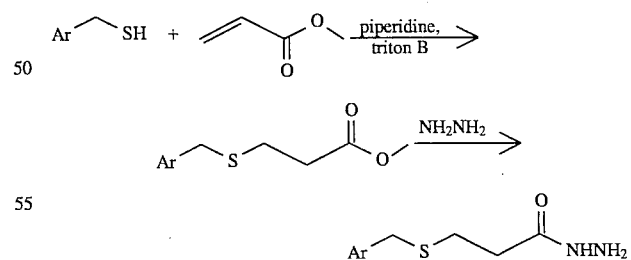

GENERAL REACTION SCHEME NO. 12

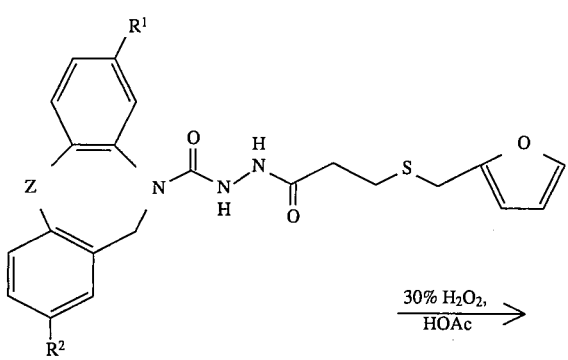

GENERAL REACTION SCHEME NO. 13

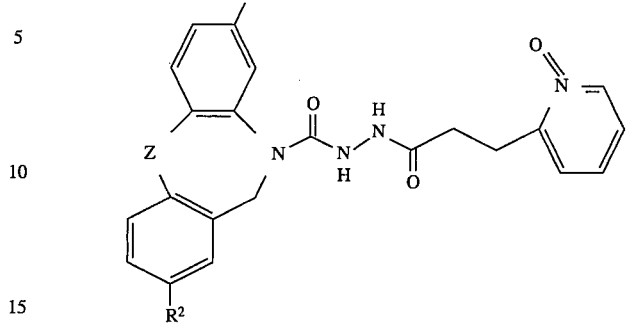

GENERAL REACTION SCHEME NO. 13

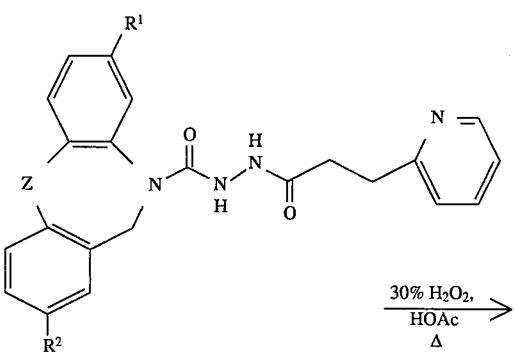

GENERAL REACTION SCHEME NO. 14

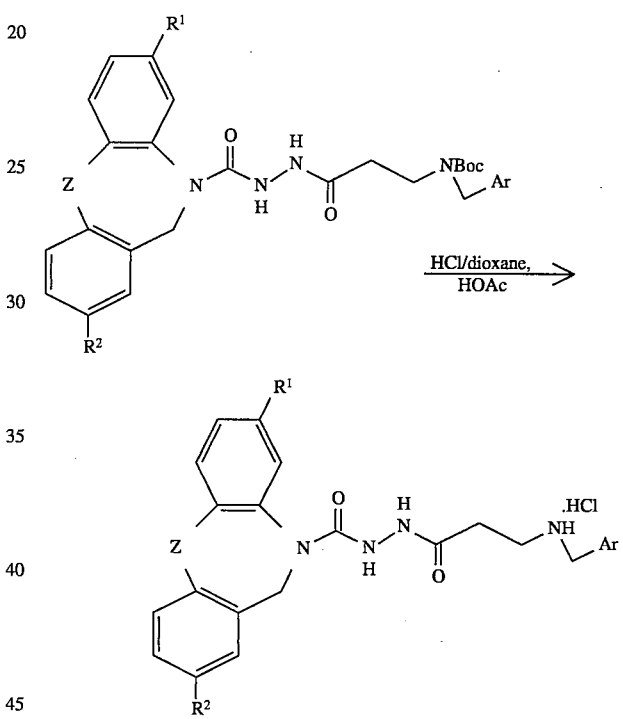

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more subdoses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of Pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and ingectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as Polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous ingection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tonque; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

Unless stated otherwise in the examples, all equipment employed in the examples is commercially available.

All starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wis.).

All patents and publications referred to in the examples, and throughout the specification, are hereby incorporated herein by reference, without admission that such is prior art.

EXAMPLE 1

8-chlorodibenz[b,f][1,4]oxazepine-10(11M)-carboxylic acid, hydrazide (1)

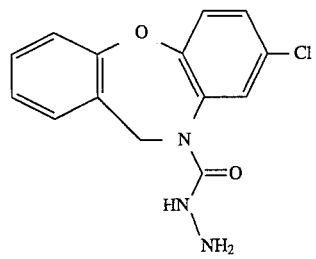

8-chlorodibenz[b,f][1,4]oxazepine-10(11H)-carboxylic acid, hydrazide (1) was synthesized in the manner described in U.S. Pat. No. 3,534,019.

To a solution of 7.3 parts of 100% hydrazine hydrate in 40 parts of ethanol was added, at 5°–10° C. with stirring, a solution of 13.0 parts of 8-chlorodibenz[b,f][1,4]-oxazepine-10(11H)carbonyl chloride (2) in 200 parts by volume of a 1:1 ethermethylene chloride solution. When the addition was complete, the mixture was allowed to warm to room temperature and was stirred for 1 hour. The mixture was then filtered and the solvent was evaporated from the filtrate. The resultant residue was then dissolved in chloroform, and the resulting chloroform solution was washed with water and dried over magnesium sulfate. The chloroform solvent was then evaporated, and the resultant crude residue was triturated with petroleum ether to give a white solid, which was then recrystallized from ethanol.

EXAMPLE 2

8-chlorodibenz[b,f][1,4]-oxazepine-10(11H)-carbonyl chloride (2)

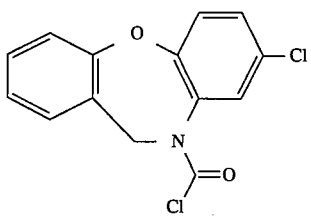

8-chlorodibenz[b,f][1,4]-oxazepine-10(11H)-carbonyl chloride (2) was also synthesized in the manner described in U.S. Pat. No. 3,534,019.

13 parts of phosgene in 45 parts of toluene was stirred for 2 hours at 5°–10° C., and then 70 parts of ether was added. This was followed by the addition of a solution of 18.9 parts of 8-chloro-10,11-dihydrodibenz[b,f][1,4]oxazepine and 7.2 parts of triethylamine in 140 parts of ether. After the addition was complete, the mixture was stirred for 2 hours, and then was filtered. The solvent was then evaporated from the filtrate. The resulting residue was then dissolved in 200 parts by volume of hot hexane, and this mixture was then filtered and cooled.

EXAMPLE 3

Ethyl 3-(2-pyridinyl)-2E-propanoate (3)

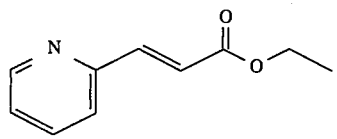

To a stirring 25 mL tetrahydrofuran (THF) solution of 0.54 g (5 mmol) of 2-pyridinecarboxaldehyde was added 1.74 g (5 mmol) of (carbethoxymethylene)triphenylphosphorane. The reaction was stirred for 24 hours. After 6 hours, the reaction had changed from a grey-green to a bright yellow color. The reaction solvent was removed under vacuum. The residue was triturated with hexanes. The solid was collected on a sintered-glass funnel. The filtrate containing the product was concentrated under reduced pressure. A quantitative yield of ethyl 3-(2-pyridinyl)-2E-propanoate (3) was recovered, and was used immediately in the manner described in Example 4, below.

EXAMPLE 4

Ethyl 3-(2-pyridinyl)propanoate (4)

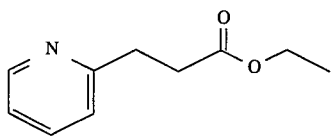

The ethyl 3-(2-pyridinyl)-2E-propanoate (3) synthesized in Example 3 above was reduced under catalytic hydrogenation conditions using 5% Pd/C in ethanol (EtOH). The yield of ethyl 3-(2-pyridinyl)propanoate (4) was 0.68 g (76%). This product was used immediately in the manner described in Example 5, below.

EXAMPLE 5

3-(2-pyridyl)propanoic acid, hydrazide (5)

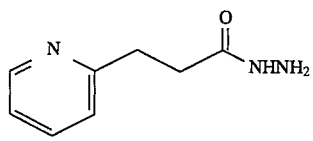

To a stirring 5 mL EtOH solution of 0.58 g (3.2 mmol) of ethyl 3-(2-pyridinyl)propanoate (4), prepared as described above in Example 4, was added 0.32 g (6.5 mmol) of hydrazine hydrate. The reaction was heated at reflux for three weeks. Although the reaction was still incomplete, the solvent was removed under vacuum. The resulting gum was triturated with diethyl ether (Et$_2$O). The product remained a gum. The yield of 3-(2-pyridyl)propanoic acid, hydrazide (5) was 0.22 g (42%). This product was used immediately in the manner described in Example 6 below.

EXAMPLE 6

8-chlorodibenz[b,f][1,4]oxazepine-10(11H)-carboxylic acid, 2-[1-oxo-3-(2-pyridinyl)propyl]hydrazide (6)

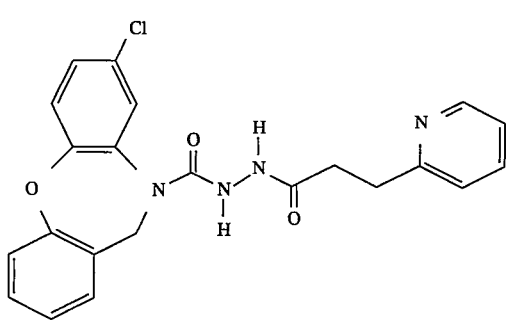

To a stirring 5 mL toluene solution of 0.22 g (1.3 mmol) of 3-(2-pyridyl)propanoic acid, hydrazide (5), prepared as described above in Example 5, and 0.18 mL (1.3 mmol) of triethylamine (TEA) was added dropwise a 5 mL toluene solution of 8-chlorodibenz[b,f][1,4]oxazepine-10(11H)-carbonyl chloride (2), prepared as described above in Example 2. The reaction was heated at reflux for 1 hour, and then the solvent was removed under vacuum. The residue was purified by column chromatography in the manner described by Still et al., *J. Org. Chem.*, 43, 2923 (1978) to yield 0.25 g (57%) of product. The identity of this material, and of the materials synthesized in the subsequent examples, was confirmed by $^1$H NMR, $^{13}$C NMR, microanalysis, and HPLC. The yield of product was 0.34 g (61%). The product was dissolved in methanol (MeOH) and filtered through activated charcoal. The solvent was removed under vacuum to obtain product. Analysis calculated for $C_{22}H_{19}N_4O_3Cl \cdot H_2O$ (M.W. 427.37): C, 61.83; H, 4.56; N, 13.11. Found: C, 61.71; H, 4.44; N, 12.89.

EXAMPLE 6A 8-chlorodibenz[b,f][1,4]oxazepine-10(11H)-carboxylic acid,
2-[1-oxo-3-(2-pyridinyl)propyl]hydrazide,
monohydrochloride (6A)

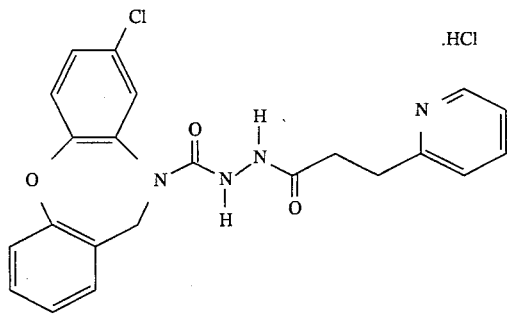

2.64 g of 8-chlorodibenz[b,f][1,4]oxazepine-10(11H)carboxylic acid, 2-[1-oxo-3-(2-pyridinyl)propyl]hydrazide (6), prepared as described above in Example 6, was taken up in 25 mL of 3A ethanol and filtered to remove any undissolved material. The solution was cooled in an ice bath with stirring. To this was added dropwise 5.3 mL of 9.5M hydrogen chloride in ethanol. After stirring in the ice bath for 5 minutes, some of the product precipitated. This was poured slowly into 275 mL of stirring diethyl ether (Et$_2$O), and the resulting mixture was stirred for 5 minutes. The resulting solid product was collected by filtration, washed with 20 mL of 3 A ethanol, followed by Et$_2$O, and dried under vacuum at 56° C. to yield 2.20 g (76.7%) of a white powder. Analysis calculated for C$_{22}$H$_{20}$N$_4$O$_3$Cl$_2$: C, 57.53; H, 4.39; N, 12,20; Cl, 15.44; Found: C, 57.31; H, 4.36; N, 11.98; Cl, 15.11.

EXAMPLE 7

8-chlorodibenz[b,f][1,4]oxazepine-10(11H)-carboxylic acid,
2-[1-oxo-3-(3-pyridinyl)-2E-propenyl]hydrazide
(7)

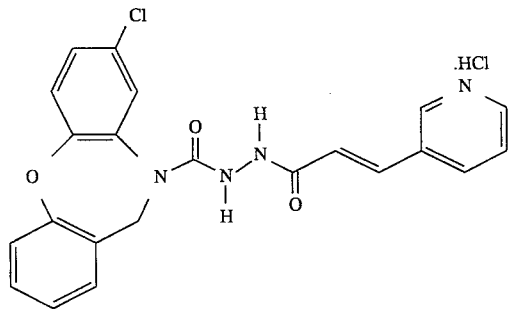

To a stirring solution of 2.82 g (9.7 mmol) of 8-chlorodibenz[b,f][1,4]oxazepine-10(11H)-carboxylic acid, hydrazide (1), prepared as described above in Example 1, in 25 mL of dimethyl formamide (DMF) cooled in an ice bath was added 1.54 g (9.7 mmol) of 3-(3-pyridyl) acrylic acid. To the hererogenous mixture was added 1.74 mL (10 mmol) of N,N-diisopropylethylamine and 1.92 g (10 mmol) of N,N-dimethylaminopropylethylcarbodiimide hydrochloride. The reaction was stirred over night at ambient temperature. To the reaction was added 100 mL of ethyl acetate (EtOAc) and 100 mL of a saturated solution of KHCO$_3$. The resulting layers were separated, and the organic layer was washed three times with saturated KHCO$_3$ and two times with water. The organic layer was then dried over Na$_2$SO$_4$ anhydrous and filtered. The solvent was removed under vacuum, and the resultant solid was chromatographed. The yield of isolated product was 2.16 g (53%). Analysis calculated for C$_{22}$H$_{17}$N$_4$O$_3$Cl (M.W. 420.86): C, 62.79; H, 4.07; N, 13.31; Cl, 8.42. Found: C, 62.72; H, 4.27; N, 12.78; Cl, 8.21.

EXAMPLE 8

8-chlorodibenz[b,f][1,4]oxazepine-10(11H)-carboxylic acid,
2-[1-oxo-3-(3-pyridinyl)propyl]hydrazide,
monohydrochloride (8)

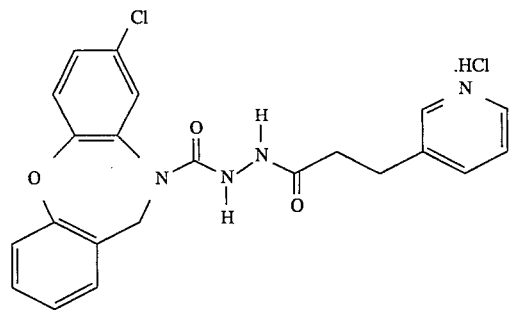

The experiment described above in Example 7 was repeated on a five mmol scale with 8-chlorodibenz[b,f][1,4]oxazepine-10(11H)-carboxylic acid, hydrazide (1), prepared as described above in Example 1, and 3-(3-pyridyl)propionic acid. The yield of the reaction product was 0.75 g (34%). The free base was dissolved in 5 mL of acetic acid (HOAc) and filtered. To the filtrate was added 5 mL of 6N HCl/dioxane. The hydrochloride salt was precipitated from the reaction by the addition of Et$_2$O. The resultant solid product was collected by filtration and dried in an Abderhalden drying pistol. Analysis calculated for C$_{22}$H$_{20}$N$_4$O$_3$Cl$_2$: C, 57.53; H, 4.39; N, 12.20; Cl, 15.44. Found: C, 57.35; H, 4.45; N, 12.08; Cl, 15.58.

EXAMPLE 9

8-chlorodibenz[b,f][1,4]oxazepine-10(11H)-carboxylic acid, 2-[1-oxo-4-(2-thienyl)butyl]hydrazide
(9)

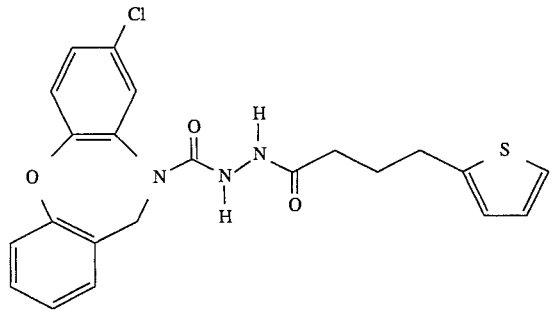

To a stirring 5 mL dichloromethane (DCM) solution of 0.29 g (one mmol) of 8-chlorodibenz[b,f][1,4]oxazepine-10(11H)-carboxylic acid, hydrazide (1), prepared as described above in Example 1, and 0.17 g (one mmol) of 4-(2-thienyl)butyric acid cooled to 5° C. was added 0.23 g (1.1 mmol) of dicyclohexylcarbodiimide. With warming to room temperature, the reaction was stirred for 18 hours. The reaction mixture was filtered through a sintered-glass funnel. The filtrate was dried under water aspirator vacuum. The resultant solid product was chromatographed as described previously. Analysis calculated for $C_{22}H_{20}N_3O_3SCl$ (M.W. 441.94): C, 59.79; H, 4.56; N, 9.51; Cl, 8.02. Found: C, 59.77; H, 4.62; N, 9.51; Cl, 8.23.

EXAMPLE 10

α,α-difluoro-β-hydroxy-3-(2-pyridinyl)-propanoic acid, hydrazide (10)

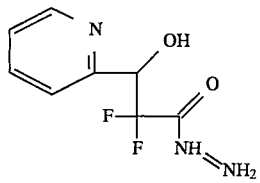

To stirring solution of 0.96 g (4.1 mmol) of ethyl 3-(2-pyridyl)-3-hydroxy-2,2-difluoropropanoate, prepared as described by Hallinan and Fried, *Tetrahedron Lett.*, 25, 2301 (1984), in 8 mL of EtOH was added 0.41 g (8.2 mmol) of hydrazine hydrate. After 16 hours, a yellow precipitate had formed. To the reaction was added $H_2O$. The precipitate was filtered and washed with a minimum of $H_2O$. The yield of product was 0.44 g (49%) after drying in a steam cabinet. Analysis calculated for $C_8H_9N_3O_2F_2$ (M.W. 217.18): C, 44.24; H, 4.18; N, 19.35. Found: C, 44.07; H, 4.16; N, 19.05.

EXAMPLE 11

8-chlorodibenz[b,f][1,4]oxazepine-10(11H)-carboxylic acid,
2-[2,2-difluoro-3-hydroxy-1-oxo-3-(2-pyridinyl)-propyl]hydrazide (11)

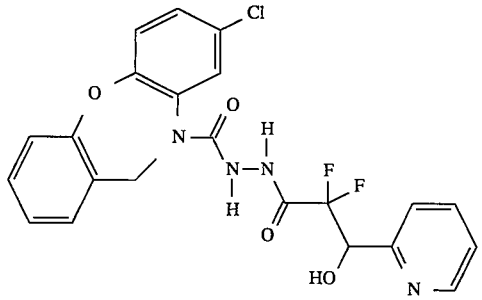

8-chlorodibenz[b,f][1,4]oxazepine-10(11H)-carboxylic acid, 2-[2,2-difluoro-3-hydroxy-1-oxo-3-(2-pyridinyl)propyl]hydrazide (11) was prepared in the manner 8-chlorodibenz[b,f]oxazepine-(10(11H)-carboxylic acid, 2-[1-oxo-3-(2-pyridinyl)propyl]hydrazide (6) was prepared, as described above in Example 6, on a 0.4 mmol scale for a yield of 0.12 g (63%). Analysis calculated for $C_{22}H_{17}N_4O_4F_2Cl.0.25\ H_2O$ (M.W. 479.36): C, 55.12; H, 3.68; N, 11.69. Found: C, 54.73; H, 3.69; N, 11.40.

EXAMPLE 11A 8-chlorodibenz[b,f][1,4]oxazepine-10(11H)-carboxylic acid,
2-[2,2-difluoro-3-hydroxy-1-oxo-3-(2-pyridinyl)-propyl]hydrazide, monohydrochloride (11A)

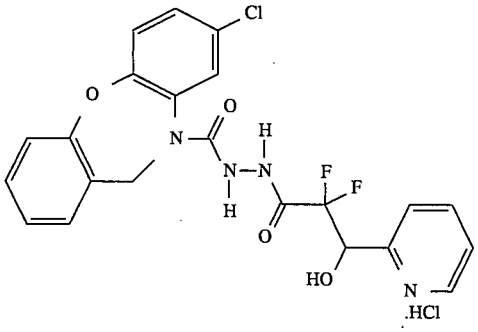

8-chlorodibenz[b,f][1,4]oxazepine-10(11H)-carboxylic acid, 2-[2,2-difluoro-3-hydroxy-1-oxo-3-(2-pyridinyl)propyl]hydrazide, monohydrochloride (11A) was prepared by dissolving 8-chlorodibenz[b,f][1,4]oxazepine-10(11H)-carboxylic acid, 2-[2,2-difluoro-3-hydroxy-1-oxo-3-(2-pyridinyl)propyl]hydrazide (11), prepared as described above in Example 11, in N HCl and lyophilizing. Analysis calculated for $C_{22}H_{17}N_4O_4F_2Cl.HCl.\ 1.2\ H_2O$ (M.W. 532.94): C, 49.58; H, 3.68; N, 10.51; Cl, 13.30. Found: C, 49.27; H, 3.65; N, 10.53; Cl, 13.01.

EXAMPLE 12

3-[(2-furanylmethyl)thio]propanoic acid, hydrazide (12)

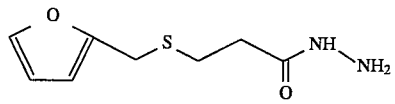

To a stirring 10 mL EtOH solution of 4.29 g (20 mmol) of ethyl 3-(furylthio)propanoate was added 0.71 g (22 mmol) of hydrazine hydrate. After heating at reflux for 24 hours, the reaction was stirred for 24 hours at room temperature. The solvent was then removed under vacuum, and the residue was dissolved in EtOH and filtered through a bed of charcoal. 2.77 g (69%) of product, which was a water white viscous liquid, was recovered and was employed immediately in the manner described in Example 13, below.

EXAMPLE 13

8-chlorodibenz[b,f][1,4]oxazepine-10(11H)-carboxylic acid,
2-[3-[(2-furanylmethyl)thio]-1-oxopropyl]hydrazide (13)

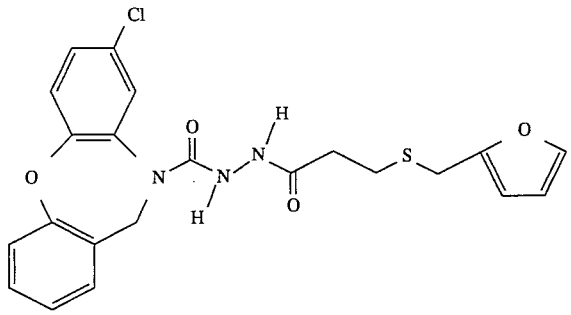

8-chlorodibenz[b,f][1,4]oxazepine-10(11H)-carboxylic acid, 2-[3-[(2-furanylmethyl)thio]-1-oxopropyl]hydrazide (13) was prepared in the manner 8-chlorodibenz[b,f]oxazepine-10(11H)carboxylic acid, 2-[1-oxo-3-(2-pyridinyl)propyl]hydrazide (6) was prepared, as described above in Example 6, from 3-[(2-furanylmethyl)thio]propanoic acid, hydrazide (12), prepared as described above in Example 12, and 8-chlorodibenz[b,f][1,4]-oxazepine-10(11H)-carbonyl chloride (2), prepared as described above in Example 2, on a 10 mmol scale. The yield was quantitative. Analysis calculated for $C_{22}H_{20}N_3O_4SCl$ (M.W. 457.94): C, 57.70; H, 4.40; N, 9.18; Cl, 7.74; S, 7.00. Found: C, 57.59; H, 4.36; N, 9.01; Cl, 7.95; S, 7.07.

EXAMPLE 14

8-chlorodibenz[b,f][1,4]oxazepine-10(11H)-carboxylic acid,
2-[1-oxo-3-(2-pyridinyl)propyl]hydrazide, N-oxide (14)

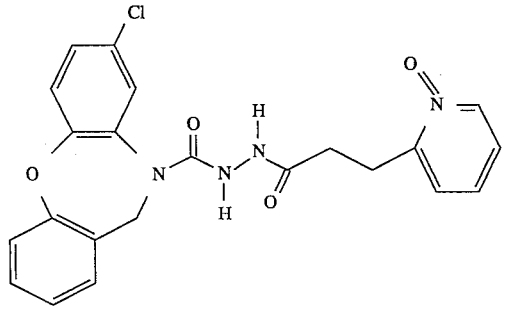

To a stirring 6 mL HOAc solution of 8-chlorodibenz[b,f]-oxazepine-10(11H)-carboxylic acid, 2-[1-oxo-3-(2-pyridinyl)propyl]hydrazide (6), prepared as described above in Example 6, was added 0.37 mL (3.62 mmol) of 30% hydrogen peroxide solution. After 1 hour of heating at 90° C., an additional 0.25 mL of 30% hydrogen peroxide solution was added. The reaction was heated for 18 hours, and then the solvent was removed under vacuum. The residue was chromatographed, and the product was recrystallized from EtOH to yield 0.083 g (9%). Analysis calculated for $C_{22}H_{19}N_4O_4Cl$ (M.W. 438.86): C, 60.21; H, 4.36; N, 12.77. Found: C, 59.88; H, 4.41; N, 12.59.

EXAMPLE 15

Methyl 3-[(2-thienylmethyl)amino]propanoate (15)

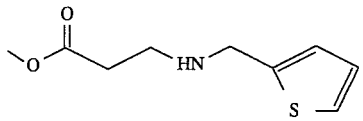

To a stirring 25 mL MeOH solution of 1.40 g (10 mmol) of methyl β-alaninate hydrochloride and 1.34 g (12 mmol) of thiophene carboxaldehyde was added 1.26 g (20 mmol) of $NaCNBH_3$. After 1 hour, 25 mL of saturated $KHCO_3$ was added to the reaction. The reaction mixture was then filtered, and the resulting filtrate was extracted with 50 mL of DCM. The organic layer was treated as described above in Example 7, and the residue was chromatographed to yield 0.60 g (30%) of product. Analysis calculated for $C_9H_{13}NO_2S$ (M.W. 199.27): C, 54.25; H, 6.58; N, 7.03. Found: C, 54.02; H, 6.63; N, 6.77.

EXAMPLE 16

3-[[(1,1-dimethylethoxy)carbonyl]-(2-thienylmethyl)-amino]-propanoic acid (16)

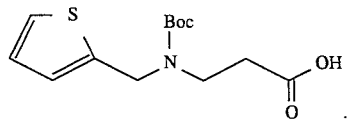

To a stirring 2 mL MeOH solution of 0.28 g (1.4 mmol) of methyl 3-[(2-thienylmethyl)amino]propanoate (15), prepared as described above in Example 15, was added 2 mL of N NaOH. After 4 hours, an additional 6 mL of N NaOH was added to the reaction. To the reaction mixture was then added 0.43 g (2.0 mmol) of di-t-butyl dicarbonate. After 16 hours, the pH was adjusted to 2 with M $KHSO_4$. The resultant solution was extracted with 3×10 mL EtOAc. The organic layer was dried over $Na_2SO_4$ anhydrous and filtered. The solvent was removed under reduced pressure. The yield of 3-[[(1,1-dimethylethoxy)carbonyl](2-thienylmethyl)amino]propanoic acid (16) was 0.34 g (85%). Analysis calculated for $Cl_3H_{19}NO_4S$ (M.W. 185.24): C, 54.72; H, 6.71; N, 4.91. Found: C, 54.55; H, 6.69; N, 4.95.

EXAMPLE 17

8-chlorodibenz[b,f][1,4]oxazepine-10(11H)-carboxylic acid, 2-[3-[[(1,1-dimethylethoxy)carbonyl](2-thienylmethyl)amino]-1-oxopropyl]hydrazide (17)

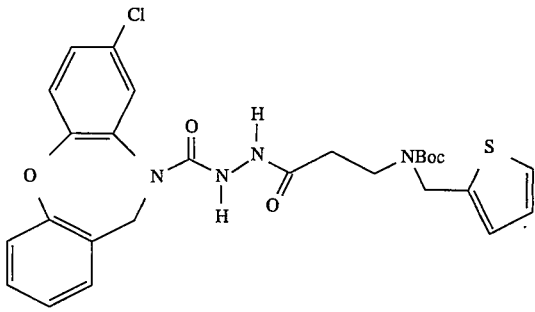

1.1 mmol of 3-[[(1,1-dimethylethoxy)carbonyl](2-thienylmethyl)amino]-propanoic acid (16), prepared as described above in Example 16, was reacted with 8-chlorodibenz[b,f][1,4]-oxazepine-10(11H)-carboxylic acid, hydrazide (1), prepared as described above in Example 1, in the same manner described in Example 9. The yield of product was 0.31 g (51%). Analysis calculated for $C_{27}H_{29}N_4O_5SCl$ 0.25 $H_2O$ (M.W. 561.57): C, 57.29.; H, 5.34; N, 9.90. Found: C, 57.42; H, 5.40; N, 9.96.

EXAMPLE 18

8-clorodibenz[b,f][1,4]oxazepine-10(11H)-carboxylic acid, 2-[1-oxo-3-(2-thienylmethyl)amino]propylhydrazide, monohydrochloride (18)

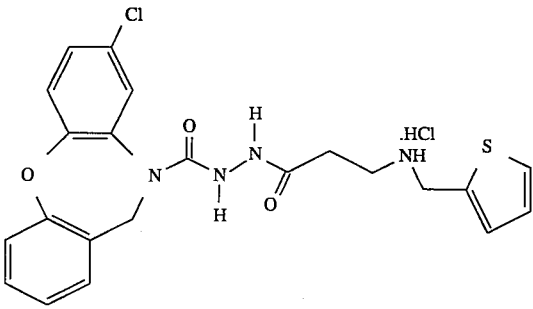

To a 2 mL HOAc solution of 0.29 g (0.5 mmol) of 8-chlorodibenz[b,f][1,4]oxazepine-10(11H)-carboxylic acid, 2-[3-[[(1,1-dimethylethoxy)carbonyl](2-thienylmethyl)amino-1-oxopropyl]hydrazide (17), prepared as described above in Example 17, was added 2 mL of 6N HCl/dioxane. After 5 minutes, the solvent was removed under reduced pressure. The resultant gum was then triturated with $Et_2O$. The white solid was filtered and was dried in a steam cabinet over night. The product was dissolved in hot $H_2O$ and the solution was filtered. The filtrate was lyophilized to yield 0.21 g (81%) of product. Analysis calculated for $C_{22}H_{21}N_4O_3SCl$ 0.25 $H_2O$ HCl (M.W. 502.42): C, 52.59; H, 4.41; N, 11.15. Found: C, 52.57; H, 4.66; N, 11.11.

EXAMPLE 19

Methyl 2-(2-thienylmethoxy)acetate (19)

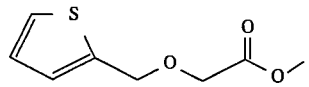

To a stirring 25 mL solution of 1.14 g (10 mmol) of thiophenemethanol in THF was added 0.24 g (10 mmol) of NaH. After the evolution of gas had ceased, 1.53 g (10 mmol) of methyl bromoacetate was added to the reaction. After 15 minutes, the reaction mixture was filtered. The solvent was removed under reduced pressure. The residue was then dissolved in 50 mL of EtOAc. The organic layer was washed with 3×50 mL of $H_2O$, and was treated in the manner described above in Example 7. The residue was chromatographed to yield 0.91 g (49%) of product. Analysis calculated for $C_8H_{10}O_3S$ (M.W. 186.23): C, 51.60; H, 5.41. Found: C, 51.41; H, 5.60.

EXAMPLE 20

2-(2-thienylmethoxy)acetic acid, hydrazide (20)

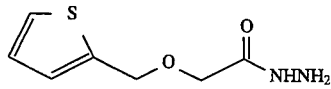

2-(2-thienylmethoxy)acetic acid, hydrazide (20) was prepared from methyl 2-(2-thienylmethoxy)acetate (19) (3.6 mmol), prepared in the manner described above in Example 19, and hydrazine (3.6 mmol) in the manner described above in Example 12 to yield 0.60 g (90%) of product.

EXAMPLE 21

8-chlorodibenz[b,f][1,4]oxazepine-10(11H)-carboxylic acid, 2-[(2-thienylmethoxy)acetyl]hydrazide (21)

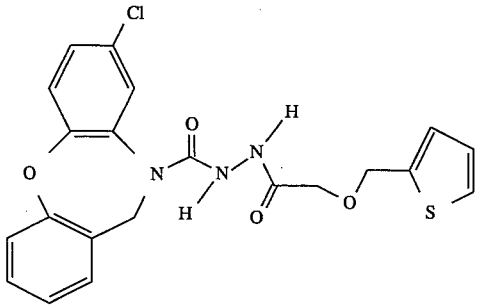

8-chlorodibenz[b,f][1,4]oxazepine-10(11H)-carboxylic acid, 2-[(2-thienylmethoxy)acetyl]hydrazide (21) was prepared in the manner described in Example 6 from 1 mmol of 2-(2-thienylmethoxy)acetic acid, hydrazide (20), prepared as described above in Example 20, and 1.0 mmol of 8-chlorodibenz[b,f][1,4]oxazepine-10(11H)-carbonyl chloride (2), prepared as described above in Example 2, to yield 0.28 g (64%) of product. Analysis calculated for $C_{21}H_{18}N_3O_4SCl$ (M.W. 443.91): C, 56.82; H, 4.09; N, 9.47. Found: C, 56.55; H, 4.08; N, 9.28.

EXAMPLE 22

Methyl 3-[(2-furanylmetyl)amino]propanoate (22)

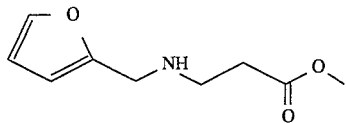

Methyl 3-[(2-furanylmethyl)amino]propanoate (22) was prepared in the manner methyl 3-[(2-thienylmethyl)amino]propanoate (15) was prepared, as described above in Example 15, on a 6.5 mmol scale from methyl β-alaninate hydrochloride and furrural to yield 0.28 g (28%) of product.

EXAMPLE 23

3-[[(1,1-dimethylethoxy)carbonyl](2-furanylmethyl)-amino]propanoic acid (23)

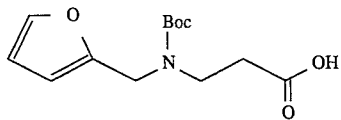

3-[[(1,1-dimethylethoxy)carbonyl](2-furanylmethyl)amino]propanoic acid (23) was prepared from methyl 3-[(2-furanylmethyl)amino]propanoate (22), prepared as described above in Example 22, and di-t-butyl dicarbonate in the same manner as 3-[[(1,1-dimethylethoxy)-carbonyl](2-thienylmethyl)amino]propanoic acid (16) was prepared, as described above in Example 16, on a 1.3 mmol scale to yield 0.17 g (49%) of product.

EXAMPLE 24

8-chlorodibenz[b,f][1,4]oxazepine-10(11H)-carboxylic acid, 2-[3-[[(1,1-dimethylethoxy)carbonyl](2-furanylmethyl)amino]-1-oxopropyl]hydrazide (24)

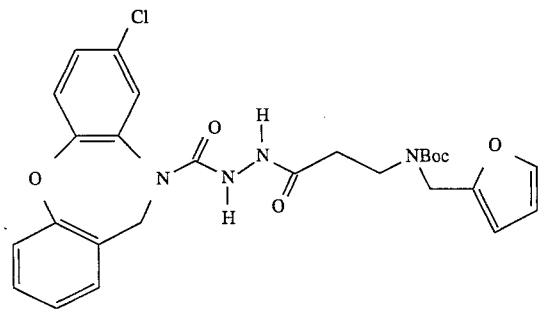

8-chlorodibenz[b,f][1,4]oxazepine-10(11H)-carboxylic acid, 2-[3-[[(1,1-dimethylethoxy)carbonyl](2-furanylmethyl)amino]-1-oxopropyl]hydrazide (24) was prepared in the same manner as 8-chlorodibenz[b,f][1,4]oxazepine-10(11H)-carboxylic acid, 2-[3-[[(1,1-dimethylethoxy)carbonyl](2-thienylmethyl)amino]-1-oxopropyl]hydrazide (17), as described above in Example 17, on a 0.63 mmol scale from 3-[[(1,1-dimethylethoxy)carbonyl](2-furanylmethyl)amino]propanoic acid (23), prepared as described above in Example 23, and 8-chlorodibenz[b,f][1,4]-oxazepine-10(11H)-carboxylic acid, hydrazide (1), prepared as described above in Example 1, to yield 0.24 g (71%) of product.

EXAMPLE 25

8-chlorodibenz[b,f][1,4]oxazepine-10(11H)-carboxylic acid, 2-[3-[(2-furanylmethyl)amino]-1-oxopropyl]hydrazide (25)

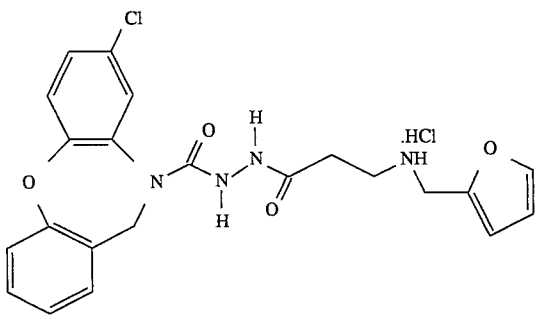

8-chlorodibenz[b,f][1,4]oxazepine-10(11H)-carboxylic acid, 2-[3-[(2-furanylmethyl)amino]-1-oxopropyl]hydrazide (25) was prepared in the same manner as 8-chlorodibenz[b,f][1,4]-oxazepine-10(11H)-carboxylic acid, 2-[1-oxo-3-[(2-thienylmethyl)amino]propylhydrazide, monohydrochloride (18), as described above in Example 18, on a 0.37 mmol scale from 8-chlorodibenz[b,f][1,4]oxazepine-10(11H)-carboxylic acid, 2-[3-[[(1,1-dimethylethoxy)carbonyl](2-furanylmethyl)amino]-1-oxopropyl]hydrazide (24), prepared as described above in Example 24, to yield 0.14 g (78%) of product. Analysis calculated for $C_{22}H_{21}N_4O_4Cl \cdot HCl \cdot 0.25 H_2O$ (M.W. 481.86): C, 54.84; H, 4.71; N, 11.63. Found: C, 54.56; H, 4.60; N, 11.33.

EXAMPLE 26

α,α-difluoro-β-hydroxy-2-thiophenepropanoic acid, hydrazide (26)

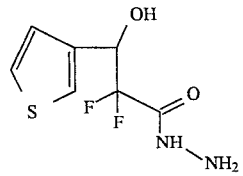

α,α-difluoro-β-hydroxy-2-thiophenepropanoic acid, hydrazide (26) was prepared in the same manner as α,α-difluoro-β-hydroxy-3-(2-pyridinyl)-propanoic acid, hydrazide (10), as described above in Example 10, on a 1.4 mmol scale from ethyl α,α-difluoro-β-hydroxy-2-thiophenepropanoate and hydrazine to yield 0.23 g (74%) of product. Analysis calculated for $C_7H_8N_2O_2F_2S$ (M.W. 222.21): C, 37.84; H, 3.63; N, 12.61. Found: C, 37.72; H, 3.51; N, 12.42.

EXAMPLE 27

8-chlorodibenz[b,f][1,4]oxazepine-10(11H)-carboxylic acid,
2-[2,2-difluoro-3-hydroxyl-1-oxo-3-(2-thienyl)-propyl]hydrazide (27)

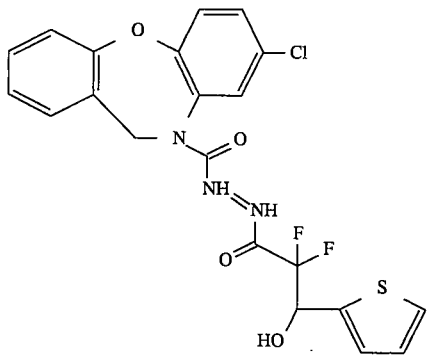

8-chlorodibenz[b,f][1,4]oxazepine-10(11H)-carboxylic acid, 2-[2,2-difluoro-3-hydroxyl-1-oxo-3-(2-thienyl)propyl]hydrazide (27) was prepared in the same manner as 8-chlorodibenz[b,f][1,4]-oxazepine-10(11H)-carboxylic acid, 2-[2,2-difluoro-3-hydroxy-1-oxo-3-(2-pyridinyl)propyl]hydrazide (11), as described above in Example 11, on a 0.9 mmol scale from α,α-difluoro-β-hydroxy-2-thiophenepropanoic acid, hydrazide (26), prepared as described above in Example 26, and 8-chlorodibenz[b,f][1,4]-oxazepine-10(11H)-carbonyl chloride (2), prepared as described above in Example 2, to yield 0.15 g (39%) of product. Analysis calculated for $C_{21}H_{16}N_3O_4SF_2Cl \cdot H_2O$ (M.W. 497.91): C, 50.66; H, 3.64; N, 8.44. Found: C, 50.89; H, 3.33; N, 8.24.

EXAMPLE 28

(2-carboxyethyl)triphenylphosphonium chloride (28)

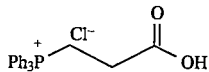

A mixture of 5.4 g (50 mmol) of 3-chloropropionic acid and 13.1 g (50 mmol) of triphenylphosphine were heated for 2 hours at 145° C. and 2 hours at 95° C. The product, a glassy solid, was dissolved in 200 mL of $CHCl_3$, to which was added 100 mL of $Et_2O$. The volume was reduced to 250 mL. 5 mL of acetone was added to the solution. After 2 hours, 10.98 g of a solid was collected and used immediately in the manner described in Example 29, below.

EXAMPLE 29

4-(3-thienyl)-3-butenoic acid (29)

To a stirring suspension of 1.60 g (67 mmol) of NaH in 20 mL of THF cooled to −60° C. was added a solution of 12.36 g (33 mmol) of (2-carboxyethyl)triphenylphosphonium chloride (28), prepared in the manner described above in Example 28, and 3.75 g (33 mmol) of 3-thiophene carboxaldehyde in 40 mL of dimethylsulfoxide (DMSO)/THF (3:1). The reaction was stirred for 16 hours at −20° C., and then for 6 hours at 0° C. The reaction was then added to cold $H_2O$. The pH was adjusted to 2 with 2N HCl. The aqueous layer was extracted with 4×200 mL of EtOAc. The organic layer was treated as described above in Example 14 and chromatographed to yield 3.41 g (61%) of 4-(3-thienyl)-3-butenoic acid (29).

EXAMPLES 30 and 31

8-chlorodibenz[b,f][1,4]oxazepine-10(11H)-carboxylic acid,
2-[1-oxo-4-(3-thienyl)-3E-butenyl]hydrazide (30) (trans)

8-chlorodibenz[b,f][1,4]oxazepine-10(11H)-carboxylic acid,
2-[1-oxo-4-(3-thienyl)-3Z-butenyl]hydrazide (31) (cis)

trans

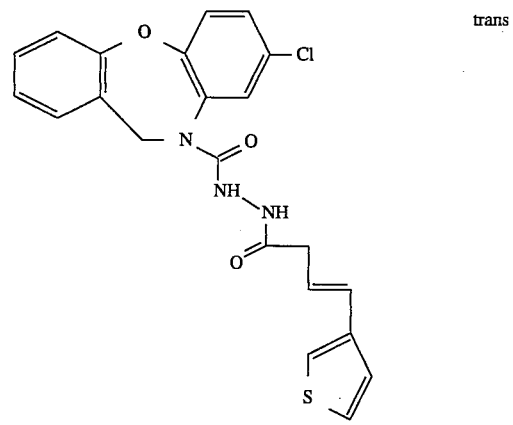

cis

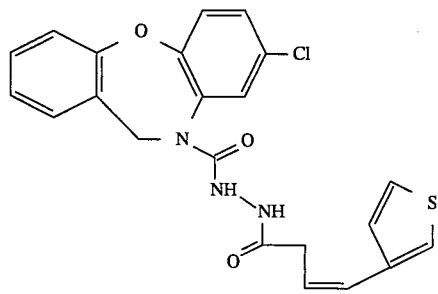

8-chlorodibenz[b,f][1,4]oxazepine-10(11H)-carboxylic acid, 2-[1-oxo-4-(3-thienyl)-3E-butenyl]hydrazide (trans) (30) and 8-chlorodibenz[b,f][1,4]oxazepine-10(11H)-carboxylic acid, 2-[1-oxo-4-(3-thienyl)-3Z-butenyl]hydrazide (cis) (31) were prepared in the manner described in Example 7 on a 5.2 mmol scale from 4-(3-thienyl)-3-butenoic acid (29), prepared as described above in Example 29, and 8-chlorodibenz[b,f][1,4]oxazepine-10(11H)-carboxylic acid, hydrazide (1), prepared as described above in Example 1, to yield 33% trans and 14% cis products after separation by column chromatography.

Trans (30)

Analysis calculated for $C_{21}H_{18}N_3O_3SCl$ (M.W. 439.92): C, 60.07; H, 4.12; N, 9.55; Cl, 8.06; S, 7.29. Found: C, 59.72; H, 4.17; N, 9.40; Cl, 8.18; S, 7.35.

Cis (31)

37

Analysis calculated for $C_{21}H_{18}N_3O_3SCl$ (M.W. 439.92): C, 60.07; H, 4.12; N, 9.55; Cl, 8.06; S, 7.29. Found: C, 59.83; H, 4.12; N, 9.55; Cl, 8.17; S, 7.38.

EXAMPLE 32

3-thiophenebutanoic acid (32)

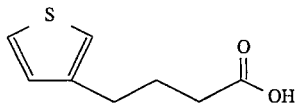

3-thiophenebutanoic acid (32) was prepared in the manner described in Example 4 on a 20 mmol scale from 4-(3-thienyl)-3-butanoic acid (29), prepared in the manner described above in Example 29, to yield 3.23 g (94%) of product.

EXAMPLE 33

8-chlorodibenz[b,f][1,4]oxazepine-10(11H)-carboxylic acid, 2-[1-oxo-4-(3-thienyl)butyl]hydrazide (33)

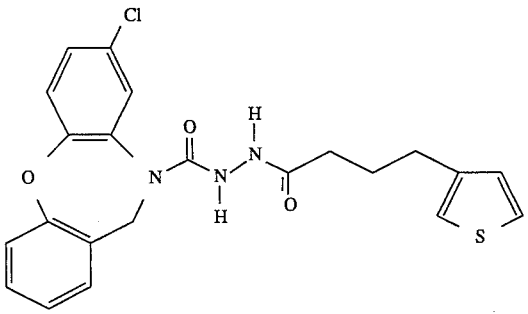

8-chlorodibenz[b,f][1,4]oxazepine-10(11H)-carboxylic acid, 2-[1-oxo-4-(3-thienyl)butyl]hydrazide (33) was prepared in the manner described in Example 7 on a 5.2 mmol scale from 3-thiophenebutanoic acid (32), prepared as described above in Example 32, and 8-chlorodibenz[b,f][1,4]oxazepine-10(11H)-carboxylic acid, hydrazide (1), prepared as described above in Example 1, to yield 0.87 g (37%) product. Analysis calculated for $C_{22}H_{20}N_3O_3SCl$ (M.W. 441.94): C, 59.79; H, 4.56; N, 9.51; Cl, 8.02. Found: C, 59.76; H, 4.58; N, 9.54; Cl, 8.06; S, 7.25.

EXAMPLE 34

8-chlorodibenz[b,f][1,4]oxazepine-10(11H)-carboxylic acid, 2-(4-pyridinylcarbonyl)hydrazide, monohydrochloride (34)

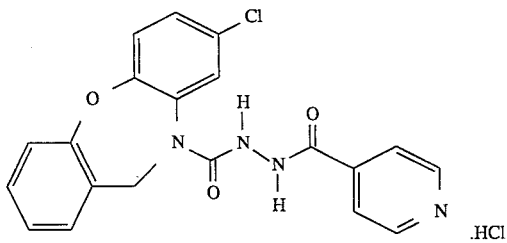

38

To a solution of 8-chlorodibenz[b,f][1,4]oxazepine-10(11H)-carboxylic acid, hydrazide (1) (1.0 g, 3.5 mmol), prepared as described above in Example 1, and methyl isonicotinate (500 mg, 3.6 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 1.62 g of crude product. The product was chromatographed (medium pressure liquid chromatography (MPLC), silica gel, $CHCl_3$:MeOH:$NH_4OH$, 95:5:05) to yield 1.0 g (72.3%) of product as the free base.

To a solution of the free base (1.0 g) in EtOH (25 mL) was added HCl in EtOH (9.5M, 5 mL), and the solvent volume was reduced under vacuum. A white precipitate formed and was collected by filtration to yield 8-chlorodibenz[b,f][1,4]-oxazepine-10(11H)-carboxylic acid, 2-(4-pyridinylcarbonyl)hydrazide, monohydrochloride (34) (740 mg). Differential Scanning Calorimetry (DSC) 146.58° C. Analysis calculated for $C_{20}H_{15}N_4O_3Cl$·HCl: C: 55.70; H: 3.74; N: 12.99; Cl: 16.44. Found: C: 55.39; H: 4.13; N: 12.24; Cl: 16.20.

EXAMPLE 35

8-chlorodibenz[b,f][1,4]oxazepine-10(11H)-carboxylic acid, 2-(3-pyridinylcarbonyl)hydrazide, monohydrochloride (35)

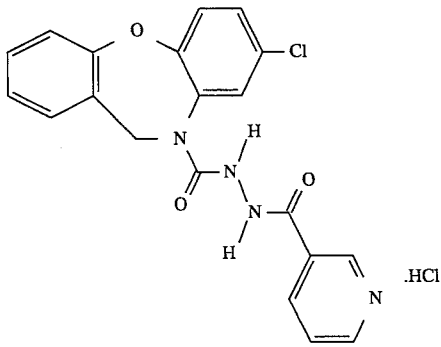

To a solution of 8-chlorodibenz[b,f][1,4]oxazepine-10(11H)-carboxylic acid, hydrazide (1) (1.0 g, 3.5 mmol), prepared as described above in Example 1, and methyl nicotinate (500 mg, 3.6 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 1.0 g of crude product. The product was chromatographed (MPLC, silica gel, $CHCl_3$:MeOH:$NH_4OH$, 95:5:0.5) to yield 650 mg (48%) of product as the free base.

To a solution of the free base (650 mg) in EtOH (25 mL) was added HCl in EtOH (9.5M, 5 mL), and the solvent volume was reduced under vacuum. A white precipitate formed and was collected by filtration to yield 8-chlorodibenz[b,f][1,4]-oxazepine-10(11H)-carboxylic acid, 2-(3-pyridinylcarbonyl)hydrazide, monohydrochloride (35) (540 mg). DSC 192.35° C. Analysis calculated for $C_{20}H_{15}N_4O_3Cl\cdot HCl$: C: 55.70; H: 3.74; N: 12.99; Cl: 16.44. Found: C: 55.76; H: 3.71; N: 12.96; Cl: 16.18.

EXAMPLE 36

8-chlorodibenz[b,f][1,4]oxazepine-10(11H)-carboxylic acid, 2-(2-pyridinylcarbonyl)hydrazide, monohydrochloride (36)

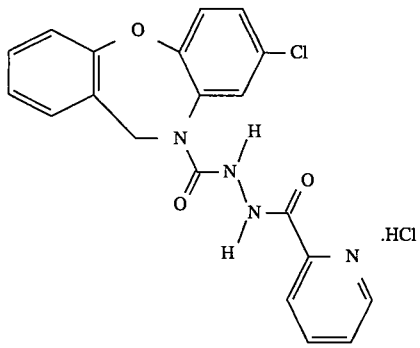

To a solution of 8-chlorodibenz[b,f][1,4]oxazepine-10(11H)-carboxylic acid, hydrazide (1) (1.0 g, 3.5 mmol), prepared as described above in Example 1, and methyl picolinate (500 mg, 3.6 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 1.0 g of crude product as an oil. The product was chromatographed (MPLC, silica gel, $CHCl_3$:MeOH:$NH_4OH$, 95:5:0.5) to yield 500 mg of a white foam (36%) product as the free base.

To a solution of the free base (500 mg) in EtOH (10 mL) was added HCl in EtOH (9.5M, 2 mL), and the solvent volume was reduced. A white precipitate formed and was collected by filtration to yield 8-chlorodibenz[b,f][1,4]oxazepine-10(11H)-carboxylic acid, 2-(2-pyridinylcarbonyl)hydrazide, monohydrochloride (36) (353 mg). DSC 133.56° C. Analysis calculated for $C_{20}H_{15}N_4O_3Cl\cdot HCl\cdot 0.1$ EtOH: C: 55.35; H: 4.65; N: 11.74; Cl: 14.85. Found: C: 55.29; H: 4.72; N: 11.76; Cl: 14.90.

EXAMPLE 37

8-chlorodibenz[b,f][1,4]oxazepine-10(11H)-carboxylic acid, 2-[(5-butyl-2-pyridinyl)carbonyl]hydrazide, monohydrochloride (37)

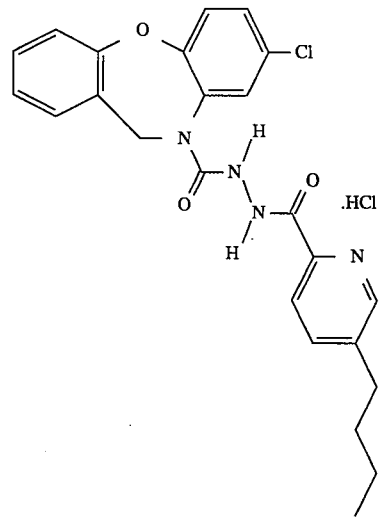

To a solution of fusaric acid (1.0 g, 5.6 mmol) in toluene (50 mL) was added oxalyl chloride (1.0 mL, 7 mmol). The resulting solution was stirred for 1 hour, followed by the removal of the solvent under reduced pressure. A solution of 8-chlorodibenz[b,f][1,4]oxazepine-10(11H)-carboxylic acid, hydrazide (1) (1.6 g, 5.5 mmol), prepared as described above in Example 1, in DCM (65 mL) and TEA (5 mL) was added to the residue. The resulting solution was stirred under $N_2$ for 16 hours. To the reaction mixture was added $CHCl_3$ (300 mL). This was followed by extraction with $NaHCO_3$ (saturated, 2×200 mL) and brine (saturated, 2×200 mL), drying over $Na_2SO_4$ and evaporation to yield 1.90 g of a tan solid. The product was chromatographed (MPLC, silica gel, $CHCl_3$:MeOH:$NH_4OH$, 95:5) to yield 1.0 g (41%) of product as the free base.

To a solution of the free base (1.0 g) in EtOH (25 mL) was added HCl in EtOH (9.5M, 5 mL), and the solvent volume was reduced. A white precipitate formed and was collected by filtration to yield 8-chlorodibenz[b,f][1,4]oxazepine-10(11H)-carboxylic acid, 2-[(5-butyl-2-pyridinyl)carbonyl]hydrazide, monohydrochloride (37) (960 mg). DSC 96.97° C. Analysis calculated for $C_{24}H_{23}N_4O_3Cl\cdot HCl$: C: 59.15; H: 4.96; N: 11.50; Cl: 14.55. Found: C: 59.33; H: 4.90; N: 11.36; Cl: 12.98.

EXAMPLE 38

8-chlorodibenz[b,f][1,4]oxazepine-10(11H)-carboxylic acid, 2-[1-oxo-3-(2-pyridinyl)-2E-propenyl]hydrazide, monohydrochloride (38)

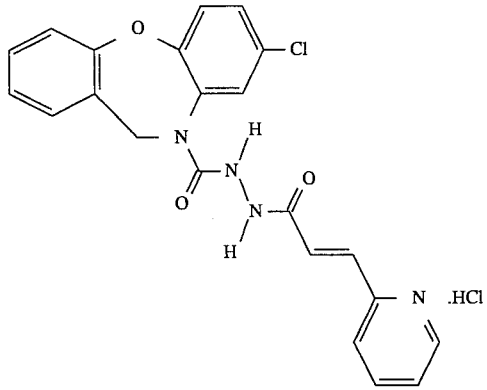

To a solution of 8-chlorodibenz[b,f][1,4]oxazepine-10(11H)-carboxylic acid, hydrazide (1) (1.5 g, 5.18 mmol), prepared as described above in Example 1, and ethyl 3-(2-pyridinyl)-2E-propanoate (3) (1.3 g, 7.34 mmol), prepared as described above in Example 3, in toluene (250 mL) was added trimethyl aluminum (12 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 2.48 g of crude product.

The crude product was chromatographed (MPLC, silica gel, $CHCl_3$:MeOH:$NH_4OH$, 95:5:0.5) to yield 900 mg (41%) of product as the free base.

To a solution of the free base (900 mg) in EtOH (25 mL) was added HCl in EtOH (9.5M, 5 mL), and the solvent volume was reduced. A white precipitate formed and was collected by filtration to yield 8-chlorodibenz[b,f][1,4]oxazepine-10(11H)-carboxylic acid, 2-[1-oxo-3-(2-pyridinyl)-2E-propenyl]hydrazide, monohydrochloride (38) (830 mg). DSC 92.21° C. Analysis calculated for $C_{22}H_{17}N_4O_3Cl \cdot HCl \cdot 0.25 H_2O$: C: 57.21; H: 4.04; N: 12.13; Cl: 15.35. Found: C: 57.02; H: 4.09; N: 11.75; Cl: 15.26.

EXAMPLE 39

8-chlorodibenz[b,f][1,4]oxazepine-10(11H)-carboxylic acid, 2-(2-pyridinylacetyl)hydrazide, monohydrochloride (39)

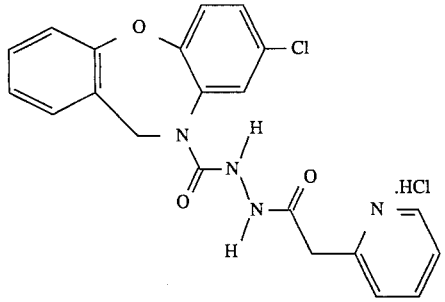

To a solution of 8-chlorodibenz[b,f][1,4]oxazepine-10(11H)-carboxylic acid, hydrazide (1) (1.0 g, 3.5 mmol), prepared as described above in Example 1, and methyl 2-pyridylacetate (560 mg, 3.7 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 2.12 g of crude product.

The crude product was chromatographed (MPLC, silica gel, $CHCl_3$:MeOH:$NH_4OH$, 95:5:0.5) to yield 520 mg (36%) of product as the free base.

To a solution of the free base (520 mg) in EtOH (25 mL) was added HCl in EtOH (9.5M, 5 mL), and the solvent volume was reduced. A white precipitate formed and was collected by filtration to yield 8-chlorodibenz[b,f][1,4]oxazepine-10(11H)-carboxylic acid, 2-(2-pyridinylacetyl)hydrazide, monohydrochloride (39) (350 mg). DSC 194.85° C. Analysis calculated for $C_{24}H_{23}N_4O_3Cl \cdot HCl \cdot 0.25 H_2O$: C: 56.07; H: 4.15; N: 12.46; Cl: 15.92. Found: C: 55.76; H: 4.28; N: 12.07; Cl: 15.76.

EXAMPLE 40

8-chlorodibenz[b,f][1,4]oxazepine-10(11H)-carboxylic acid, 2-(3-pyridinylacetyl)hydrazide, monohydrochloride (40)

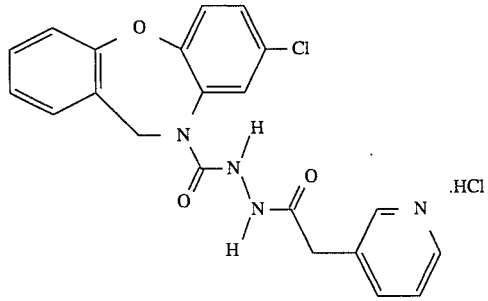

To a solution of 8-chlorodibenz[b,f][1,4]oxazepine-10(11H)-carboxylic acid, hydrazide (1) (1.0 g, 3.5 mmol), prepared as described above in Example 1, and ethyl 3-pyridylacetate (570 mg, 3.6 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 900 mg of crude product.

The crude product was chromatographed (MPLC, silica gel, $CHCl_3$:MeOH:$NH_4OH$, 95:5:0.5) to yield 260 mg (18%) of product as the free base.

To a solution of the free base (260 mg) in EtOH (25 mL) was added HCl in EtOH (9.5M, 5 mL), and the solvent volume was reduced. A white precipitate formed and was collected by filtration to yield 8-chlorodibenz[b,f][1,4]oxazepine-10(11H)-carboxylic acid, 2-(3-pyridinylacetyl)hydrazide, monohydrochloride (40) (117 mg). DSC 196.68° C. Analysis calculated for $C_{21}H_{17}N_4O_3Cl.1.2$ HCl: C: 55.73; H: 4.05; N: 12.38; Cl: 17.23. Found: C: 55.51; H: 4.18; N: 12.38; Cl: 16.73.

EXAMPLE 41

8-chlorodibenz[b,f][1,4]oxazepine-10(11H)-carboxylic acid, 2-(4-pyridinylacetyl)hydrazide, monohydrochloride (41)

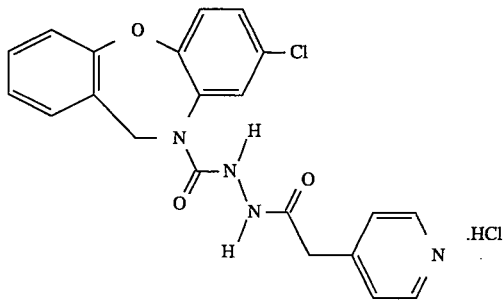

To a solution of 8-chlorodibenz[b,f][1,4]oxazepine-10(11H)-carboxylic acid, hydrazide (1) (1.0 g, 3.5 mmol), prepared as described above in Example 1, and ethyl 4-pyridylacetate (520 mg, 3.6 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were combined, dried ($Na_2SO_4$) and evaporated to yield 600 mg of crude product. The product was chromatographed (MPLC, silica gel, $CHCl_3$:MeOH:$NH_4OH$, 95:5:0.5) to yield 260 mg (18%) of product as the free base.

To a solution of the free base (260 mg) in EtOH (25 mL) was added HCl in EtOH (9.5M, 5 mL), and the solvent volume was reduced. A white precipitate formed and was collected by filtration to yield 8-chlorodibenz [b,f][1,4]oxazepine-10(11H)-carboxylic acid, 2-(4-pyridinylacetyl)hydrazide, monohydrochloride (41) (70 mg). DSC 186.14° C. Analysis calculated for $C_{21}H_{17}N_4O_3Cl.1.1$ HCl.0.75 $H_2O$: C: 54.54; H: 4.27; N: 12.12; Cl: 16.10. Found: C: 55.76; H: 3.71; N: 12.96; Cl: 16.18.

EXAMPLE 42

Ethyl 3-(4-pyridinyl)-2E-propanoate (42)

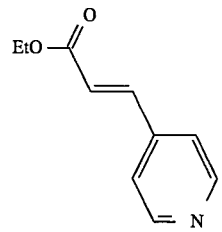

To a stirring 25 mL THF solution of 0.54 g (5 mmol) of 4-pyridinecarboxaldehyde was added 1.74 g (5 mmol) of (carbethoxymethylene)triphenylphosphorane. The reaction was stirred for 24 hours. After 6 hours, the reaction had changed from a grey-green to a bright yellow. The reaction solvent was then removed under vacuum. The residue was triturated with hexanes, and then the solid was filtered onto a sintered-glass funnel. The filtrate was subjected to reduced pressure to remove the solvent from the product. A quantitative yield of ethyl 3-(4-pyridinyl)-2E-propanoate (42) was recovered.

EXAMPLE 43

Ethyl 4-pyridinepropanoate (43)

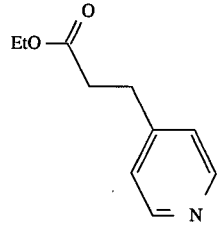

The ethyl 3-(4-pyridinyl)-2E-propanoane (42) prepared in Example 42 was reduced under catalytic hydrogenation conditions using 5% Pd/C. The yield of the resulting ethyl 4-pyridinepropanoate (43) was 0.68 g (76%).

EXAMPLE 44

8-chlorodibenz[b,f][1.4]oxazepine-10(11H)-carboxylic acid, 2-[1-oxo-3-(4-pyridinyl)propyl]hydrazide, monohydrochloride (44)

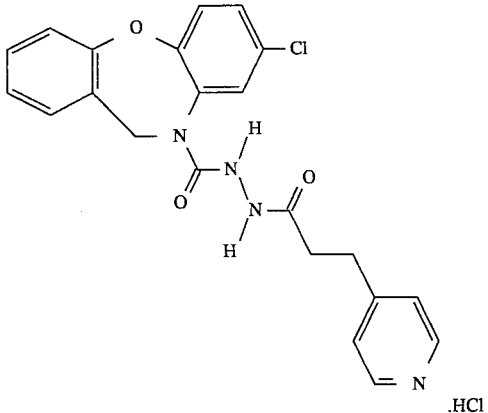

.HCl

To a solution of 8-chlorodibenz[b,f][1,4]oxazepine-10(11H)-carboxylic acid, hydrazide (1) (1.0 g, 3.5 mmol), prepared as described above in Example 1, and ethyl 4-pyridyl propanoate (614 mg, 3.6 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1M, 2×200 mL), and the aqueous extracts were combined and extracted with EtOAc (3×200 mL). The organic solutions were then combined, dried ($Na_2SO_4$) and evaporated.

The resulting product was chromatographed (MPLC, silica gel, $CHCl_3$:MeOH:$NH_4OH$, 95:5:0.5) to yield 350 mg (24%) of product as the free base.

To a solution of the free base (350 mg) in EtOH (25 mL) was added HCl in EtOH (9.5M, 5 mL), and the solvent volume was reduced. A white precipitate formed and was collected by filtration to yield 8-chlorodibenz[b,f][1,4]oxazepine-10(11H)-carboxylic acid, 2-[1-oxo-3-(4-pyridinyl)propyl]hydrazide, monohydrochloride (44) (217 mg). DSC 183.75°. Analysis calculated for $C_{21}H_{17}N_4O_3Cl \cdot HCl \cdot H_2O$: C: 55.24; H: 4.59; N: 11.71; Cl: 15.57. Found: C: 54.86; H: 4.65; N: 12.21; Cl: 15.97.

EXAMPLE 45

8-chlorodibenz[b,f][1,4oxazepine-10(11H)-carboxylic acid, 2-[1-oxo-3-(4-pyridinyl)-2E-propenyl]hydrazide, monohydrochloride (45)

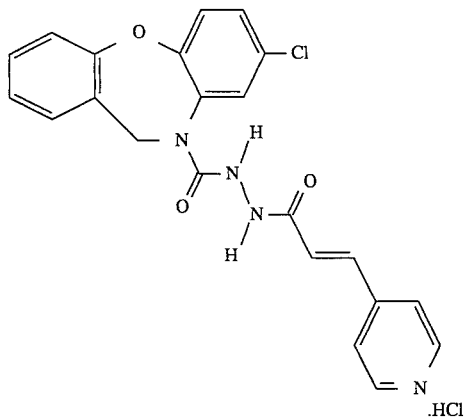

.HCl

To a solution of 8-chlorodibenz[b,f][1,4]oxazepine-10(11H)-carboxylic acid, hydrazide (1) (1.0 g, 3.5 mmol), prepared as described above in Example 1, and ethyl 4-pyridylpropanoate (620 mg, 3.5 mmol) in toluene (250 mL) was added trimethyl aluminum (8.0 mmol). The resulting yellow solution was refluxed under a $N_2$ atmosphere for 16 hours. The reaction mixture was allowed to cool to room temperature, followed by the addition of methanol (7 mL). The reaction mixture was extracted with NaOH (1 M, 2×200 mL), and the aqueous extracts were combined and extracted with EtOAc (3×200 mL). The organic solutions were combined, dried ($Na_2SO_4$) and evaporated to yield 1.29 g of crude product. The product was chromatographed (MPLC, silica gel, $CHCl_3$:MeOH:$NH_4OH$, 95:5:0.5) to yield 330 mg (23%) of product as the free base.

Toga solution of the free base (330 mg) in EtOH (25 mL) was added HCl in EtOH (9.5M, 5 mL), and the solvent volume was reduced. A white precipitate formed and was collected by filtration to yield 8-chlorodibenz[b,f][1,4]oxazepine-10(11H)-carboxylic acid, 2-[1-oxo-3-(4-pyridinyl)-2E-propenyl]hydrazide, monohydrochloride (45) (290 mg). DSC 113.49° C. Analysis calculated for $C_{22}H_{17}N_4O_3Cl \cdot 1$ HCl: C: 57.78; H: 3.97; N: 12.25. Found: C: 57.28; H: 4.01; N: 12.17.

EXAMPLE 46

4-(2-pyridyl)butanoic acid (46)

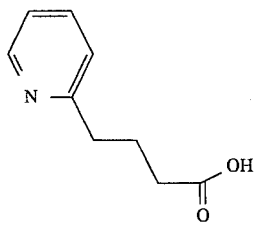

Diethyl β-(2-pyridyl)-ethylmalonate was prepared in the manner described by V. Boekelheide and S. Rothchild, *JACS*, 71, 879 (1949). Briefly, diethyl malonate (375 g, 2.35 moles) was added to a solution of sodium ethoxide (23 g of sodium in 225 mL of absolute alcohol). To the boiling mixture, freshly distilled 2-vinylpyridine (106 g, 1.0 mole) in 175 mL of absolute alcohol was added slowly. After the mixture had boiled under reflux for two hours, the alcohol was removed by distillation and the residue was acidified with dilute hydrochloric acid. The unreacted malonic ester was extracted with ether, the aqueous phase was made basic with dilute sodium hydroxide, and the basic organic layer was extracted with ether. After the ethereal solution had been dried over Drierite, the ether and recovered 2-vinylpyridine (boiling point 58° C. at 16 mm) were removed in vacuo.

A solution of diethyl β-(2-pyridyl)-ethylmalonate (25 g, 94 mmol) in ethanol (100 mL) and NaOH (1M, 200 mL) was refluxed for 2 hours. The ethanol was removed by distillation, and the solution was acidified with concentrated $H_2SO_4$. The resulting solution was refluxed for 30 minutes, and then the pH was adjusted to 4. The solvent was removed and the residue was dried under vacuum. The residue was suspended in ethanol and filtered. The ethanol was removed to yield 4-(2-pyridyl)butanoic acid (46) (12 g).

EXAMPLE 47

8-chlorodibenz[b,f][1,4]oxazepine-10(11H)-carboxylic acid, 2-[1-oxo-4-(2-pyridinyl)buty]hydrazide, monohydrochloride (47)

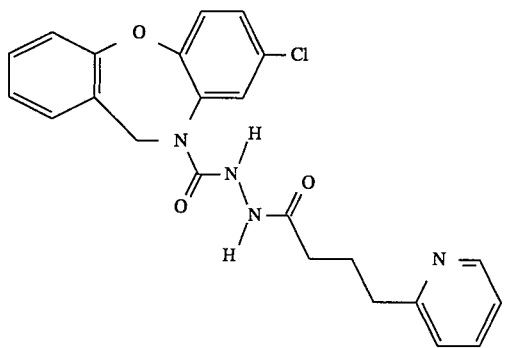

To a stirring solution of 4-(2-pyridyl)butanoic acid (46) (1.0 g, 6 mmol), prepared as described above in Example 46, in DMF (50 mL) under an Ar atmosphere was added carbonyl diimidazole (1.1 g, 6.8 mmol). The reaction solution was stirred for 15 minutes, followed by the addition of 8-chlorodibenz[b,f][1,4]-oxazepine-10(11H)-carboxylic acid, hydrazide (1) (1.43 g, 5 mmol), prepared as described above in Example 1. The reaction solution was stirred for 16 hours, and then the solvent was removed and the residue was taken up in EtOAc (250 mL), followed by extraction with brine (125 mL), saturated $NaHCO_3$ (125 mL), and HCl (1M, 125 mL). The HCl extract was basified with NaOH (1M), extracted with EtOAc (2×125 mL) dried ($Na_2SO_4$) and evaporated to yield 500 mg of a white solid. The product was chromatographed (MPLC, silica gel, $CHCl_3$:MeOH:$NH_4OH$, 95:5:0.5) to yield 400 mg (15%) of product as the free base.

To a solution of the free base (400 mg) in EtOH (25 mL) was added HCl in EtOH (9.5M, 5 mL), and the solvent volume was reduced. A white precipitate formed and was collected by filtration to yield 8-chlorodibenz[b,f][1,4]ox- azepine-10(11H)-carboxylic acid, 2-[1-oxo-4-(2-pyridinyl)butyl]hydrazide, monohydrochloride (47) (320 mg). DSC 216.77° C. Analysis calculated for $C_{23}H_{22}N_4O_3Cl \cdot HCl \cdot 3.5 H_2O$: C: 51.50; H: 5.45; N: 10.45. Found: C: 51.32; H: 4.95; N: 10.94.

EXAMPLE 48

Methyl 4-(4-pyridyl)butanoate (48)

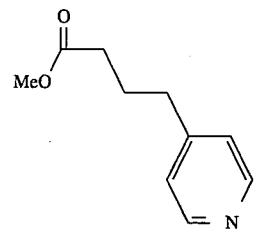

Diethyl β-(4-pyridyl)-ethylmalonate was prepared according to the method of V. Boekelheide and S. Rothchild, *JACS*, 71, 879 (1949), as described above in Example 46.

A solution of diethyl β-(4-pyridyl)-ethylmalonate (25 g, 94 mmol) in ethanol (100 mL) and NaOH (1M, 200 mL) was refluxed for 2 hours. The ethanol was removed by distillation, and the solution was acidified with concentrated $H_2SO_4$. The resulting solution was refluxed for 30 minutes, and the pH was adjusted to 4. The solvent was removed and the residue was dried under vacuum. The residue was taken up in methanol (300 mL), trimethyl orthoformate (10 mL) and $H_2SO_4$ (5 mL), and the resulting solution was refluxed for 3 hours. The solvent was removed, and the residue was taken up in $CHCl_3$ and extracted with NaOH (1M) and saturated brine, dried ($Na_2SO_4$) and evaporated to yield methyl 4-(4-pyridyl)butanoate (48) (15 g).

EXAMPLE 49

8-chlorodibenz[b,f][1,4]oxazepine-10(11H)-carboxylic acid, 2-[1-oxo-4-(4-pyridinyl)butyl]hydrazide (49)

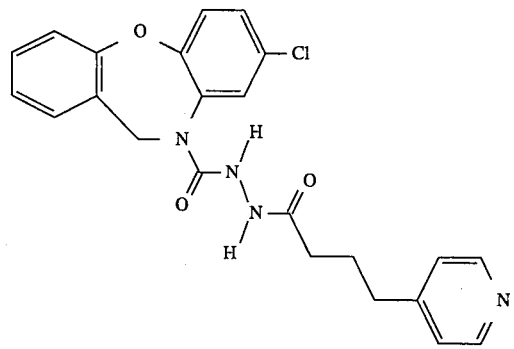

To a solution of 8-chlorodibenz[b,f][1,4]oxazepine-10(11H)-carboxylic acid, hydrazide (1) (1.5 g, 5 mmol), prepared as described above in Example 1, and methyl 4-(4-pyridyl)butanoate (48) (2.4 g, 13 mmol), prepared as described above in Example 48, in toluene (250 mL) was added dimethylaluminumchloride (20.0 mmol). The resulting yellow solution was refluxed under a $N_2$ atmosphere for 16 hours. The reaction mixture was allowed to cool to room temperature, followed by the addition of methanol (7 mL).

The reaction mixture was extracted with sodium hydroxide (1M, 2×200 mL), and the aqueous extracts were combined and extracted with ethyl acetate (3×200 mL). The organic solutions were combined, dried (Na$_2$SO$_4$) and evaporated to yield 1.8 g of crude product as a thick oil.

The crude product was chromatographed (MPLC, silica gel, CHCl$_3$:MeOH:NH$_4$OH, 95:5:0.5) to yield 1.3 g (57%) of product as the free base. The product was recrystallized with EtOH to yield 1.1 g of white crystals of 8-chlorodibenz[b,f][1,4]oxazepineine-10(11H)-carboxylic acid, 2-[1-oxo-4-(4-pyridinyl)butyl]hydrazide 49). DSC 173.33° C. Analysis calculated for C$_{23}$H$_{22}$N$_4$O$_3$Cl: C: 63.23; H: 4.85; N: 12.82; Cl: 8.12. Found: C: 62.83; H: 4.97; N: 12.59; Cl: 7.85.

EXAMPLE 50

α,α-difluoro-β-hydroxy-3-(4-pyridinyl)propanoic acid, hydrazide (50)

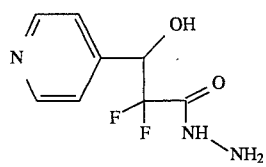

α,α-difluoro-β-hydroxy-3-(4-pyridinyl)-propanoic acid, hydrazide (50) was prepared in the manner described in Example 10 on a 20 mmol scale using ethyl α,α-difluoro-β-hydroxy-3-(4-pyridinyl)-propanoate and hydrazine to yield 2.7 g (62%) of product. This product was used immediately in the manner described in Example 51, below.

EXAMPLE 51

8-chlorodibenz[b,f][1,4]oxazepine-10(11H)-carboxylic acid,
2-[2,2-difluoro-3-hydroxy-1-oxo-3-(4-pyridinyl)-propyl]hydrazide (51)

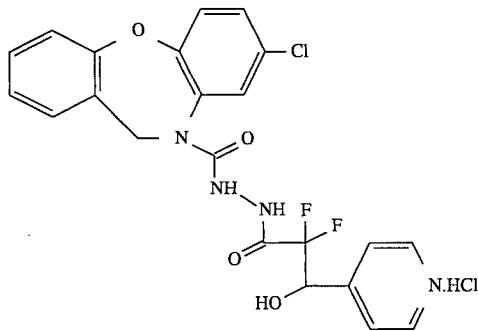

The free base of 8-chlorodibenz[b,f][1,4]oxazepine-10(11H)-carboxylic acid, 2-[2,2-difluoro-3-hydroxy-1-oxo-3-(4-pyridinyl)propyl]hydrazide (51) was prepared in the same manner as 8-chlorodibenz[b,f][1,4]oxazepine-10(11H)-carboxylic acid, 2-[1-oxo-3-(2-pyridinyl)propyl]hydrazide (6), as described above in Example 6, on a 1.75 mmol scale from α,α-difluoro-β-hydroxy-3-(4-pyridinyl)-propanoic acid, hydrazide (50), prepared in the manner described above in Example 50, and 8-chlorodibenz[b,f][1,4]-oxazepine-10(11H)-carbonyl chloride (2), prepared in the manner described above in Example 2, for a yield of 0.098 g (12%) of product. The free base was taken up in acetic acid (1.5 mL) and 1M HCl (1.5 mL). The material was lyophilized to yield 0.049 mg of the hydrochloride salt. Analysis calculated for C$_{22}$H$_{17}$N$_4$O$_4$F$_2$Cl.HCl. 0.25 H$_2$O (M.W. 514.83): C, 51.23; H, 3.62; N, 10.86. Found: C, 50.85; H, 3.67; N, 10.94.

EXAMPLE 52

Methyl 3-[(2-pyridylmethyl)thio]propanoate (52)

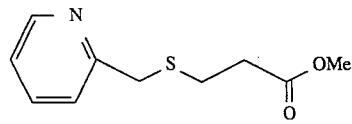

2-pyridylmethyl mercaptan, which is one of the starting materials employed in preparing methyl 3-[(2-pyridylmethyl)thio]propanoate (52), was prepared in the manner described in U.S. Pat. No. 3,069,472. Briefly, one-third mole of 2-bromoethylpyridine was reacted with one-sixth mole of calcium di-(tert-butyl)mercaptide to produce 2-pyridylmethyl tert-butyl sulfide. On hydrolysis of the 2-pyridylmethyl tert-butyl sulfide with 25% aqueous sulfuric acid, 2-pyridylmethyl mercaptan was produced.

To a stirring solution of 11.5 g (92 mmol) of 2-pyridylmethyl mercaptan and 7.94 g (92 mmol) of methyl acrylate was added 3 mL of piperidine and 3 mL of triton B. After stirring for 16 hours, the product was distilled under high vacuum. The resulting product was used immediately in the manner described in Example 53, below.

EXAMPLE 53

3-[(2-pyridylmethyl)thio]propanoic acid, hydrazide (53)

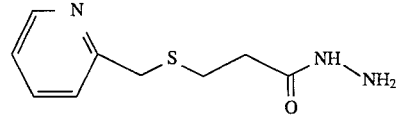

3-[(2-pyridylmethyl)thio]propanoic acid, hydrazide (53) was prepared in the manner described in Example 12 on a 14 mmol scale from methyl 3-[(2-pyridylmethyl)thio]propanoate (52), prepared as described above in Example 52, to yield 2.5 g (97%) of product.

EXAMPLE 54

8-chlorodibenz[b,f][1,4]oxazepine-10(11H)-carboxylic acid, 2-[3-[2-(pyridylmethyl)thio]-1-oxopropyl]hydrazide (54)

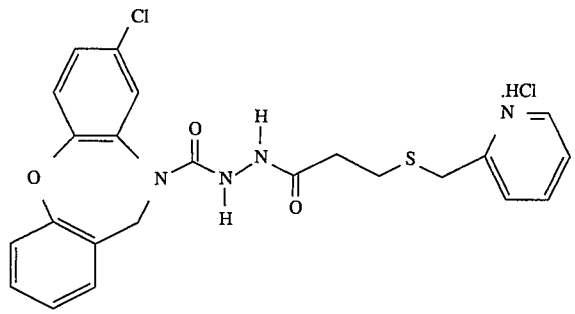

8-chlorodibenz[b,f][1,4]oxazepine-10(11H)-carboxylic acid, 2-[3-[2-(pyridylmethyl)thio]-1-oxopropyl]hydrazide (54) was prepared in the manner described in Example 6 from 3-[(2-pyridylmethyl)thio]propanoic acid, hydrazide (53), prepared as described above in Example 53, and 8-chlorodibenz[b,f][1,4]-oxazepine-10(11H)-carbonyl chloride (2), prepared as described above in Example 2, on a 4.8 mmol scale to yield 0.47 g (25%) of free base.

The free base was taken up in acetic acid and 1M HCl (1.5 mL). The material was lyophilized to yield 0.49 g of the hydrochloride salt. Analysis calculated for $C_{23}H_{27}N_4O_3SCl.0.9\ HCl.1\ H_2O$ (M.W. 519.79): C, 53.14; H, 4.63; N, 10.78; Cl, 12.96; S, 6.17. Found: C, 53.01; H, 4.72; N, 10.92; Cl, 12.83; S, 5.89.

EXAMPLE 55

Methyl 3-[(2-thienylmethyl)thio]propanoate (55)

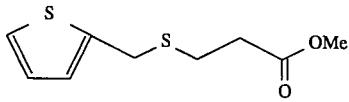

Methyl 3-[(2-thienylmethyl)thio]propanoate (55) was prepared in the manner described above in Example 52 using methyl acrylate and 2-thienylmethyl mercaptan.

EXAMPLE 56

3-[(2-thienylmethyl)thio]propanoic acid, hydrazide (56)

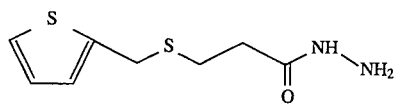

3-[(2-thienylmethyl)thio]propanoic acid, hydrazide (56) was prepared in the manner that 3-[(2-furanylmethyl)thio]propanoic acid, hydrazide (12) was prepared (Example 12) on a 23 mmol scale from methyl 3-[(2-thienylmethyl)thio]propanoate (55). After the solvent was removed under vacuum, 2.77 g (69%) of the product, which was a water white viscous liquid, was recovered and was used immediately in the manner described in Example 57, below.

EXAMPLE 57

8-chlorodibenz[b,f][1,4]oxazepine-10(11H)-carboxylic acid, 2-[3-[2-(thienylmethyl)thio]-1-oxopropyl]hydrazide (57)

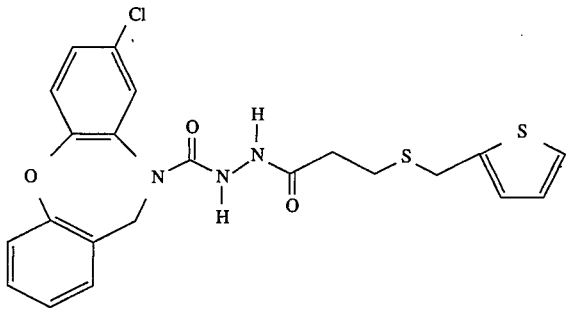

8-chlorodibenz[b,f][1,4]oxazepine-10(11H)-carboxylic acid, 2-[3-[2-(thienylmethyl)thio]-1-oxopropyl]hydrazide (57) was prepared in the manner described in Example 6 from 3-[(2-thienylmethyl)thio]propanoic acid, hydrazide (56), prepared as described above in Example 56, and 8-chlorodibenz[b,f][1,4]-oxazepine-10(11H)-carbonyl chloride (2), prepared as described above in Example 2, on a 23 mmol scale to yield 4.58 g (42%) of product. Analysis calculated for $C_{22}H_{20}N_3O_3S_2Cl$ (M.W. 473.99): C, 57.75; H, 4.25; N, 8.86; Cl, 7.48. Found: C, 55.78; H, 4.40; N, 8.77; Cl, 7.73.

EXAMPLE 58

5-(2-thienyl)pentanoic acid (58)

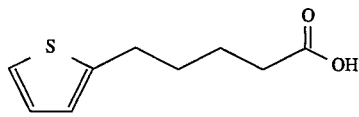

5-(2-thienyl)pentanoic acid (58) was synthesized in the same manner as 3-thiophenebutanoic acid (32), as described above in Example 32, on a 20 mmol scale from 5-(2-thienyl)-4-pentanoic acid.

EXAMPLE 59

8-chlorodiben[b,f][1,4]oxazepine-10(11H)-carboxylic acid, 2-[1-oxo-5-(2-thienyl)pentyl]hydrazide (59)

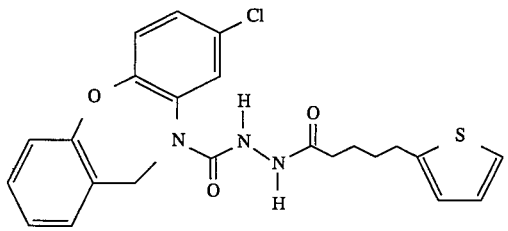

8-chlorodibenz[b,f][1,4]oxazepine-10(11H)-carboxylic acid, 2-[1-oxo-5-(2-thienyl)pentyl]hydrazide (59) was prepared in the manner described in Example 7 on a 7.6 mmol scale from 5-(2-thienyl)pentanoic acid (58), prepared as described above in Example 58, and 8-chlorodibenz[b,f][1,4]oxazepine-10(11H)-carboxylic acid, hydrazide (1), prepared as described above in Example 1. Analysis calculated for $C_{23}H_{22}N_3O_3SCl$ (M.W. 455.95): C, 60.58; H, 4.86; N, 9.22; Cl, 7.78; S, 7.03. Found: C, 60.72; H, 4.94; N, 9.22; Cl, 7.97; S, 7.08.

EXAMPLE 60

8-chlorodibenz[b,f][1,4]oxazepine-10(11H)-carboxylic acid,
2-[3-[(2-furanylmethyl)sulfinyl]-1-oxopropyl]hydrazide
(60)

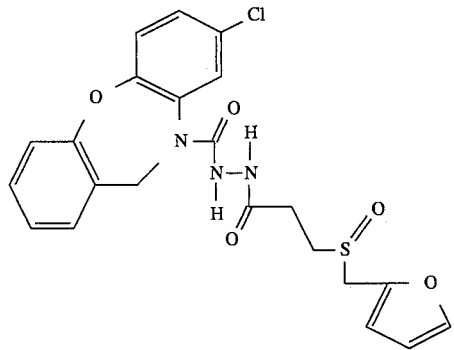

To a stirring solution of 0.69 g (1.5 mmol) of 8-chlorodibenz[b,f][1,4]oxazepine-10(11H)-carboxylic acid, 2-[3-[(2-furanylmethyl)thio]-1-oxopropyl]hydrazide (13), prepared as described above in Example 13, in 5 mL of HOAc was added 0.13 mL (1.5 mmol) of a 30% hydrogen peroxide solution. After one hour, the reaction mixture was lyophilized. The product was recrystallized from EtOAc-hexanes. The yield of 8-chlorodibenz[b,f][1,4]oxazepine-10(11H)-carboxylic acid, 2-[3-[(2-furanylmethyl)sulfinyl]-1-oxopropyl]hydrazide (60) was 0.56 g (79%). Analysis calculated for $C_{22}H_{20}N_3O_5SCl$ (M.W. 473.93): C, 55.76; H, 4.25; N, 8.87; Cl, 7.48; S, 6.77. Found: C, 55.67; H, 4.30; N, 8.79; Cl, 7.47; S, 6.56.

EXAMPLE 61

8-chlorodibenz[b,f][1,4]oxazepine-10(11H)-carboxylic acid,
2-[3-[(2-furanylmethyl)sulfonyl]-1-oxopropyl]hydrazide
(61)

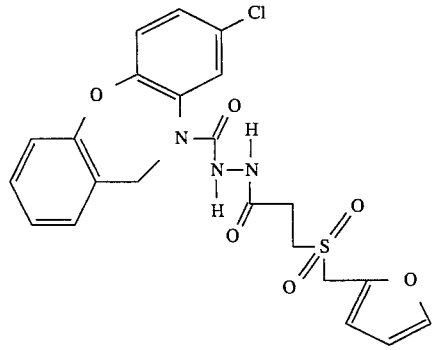

To a stirring solution of 0.76 g (1.7 mmol) of 8-chlorodibenz[b,f][1,4]oxazepine-10(11H)-carboxylic acid, 2-[3-[(2-furanylmethyl)thio]-1-oxopropyl]hydrazide (13), prepared as described above in Example 13, in 35 mL of HOAc was added 0.30 mL (3.4 mmol) of 30% hydrogen peroxide. After 2 hours of stirring at 60° C., an additional 0.30 mL of a 30% hydrogen peroxide solution was added. The reaction was heated for 19 hours at 55° C. The solvent was removed under vacuum. The product was purified by column chromatography. The yield of 8-chlorodibenz[b,f][1,4]-oxazepine-10(11H)-carboxylic acid, 2-[3-[(2-furanylmethyl)-sulfonyl]-1-oxopropyl]hydrazide (61) was 0.27 g (33%). Analysis calculated for $C_{22}H_{20}N_3O_5SCl$ (M.W. 473.93): C, 55.76; H, 4.25; N, 8.87; Cl, 7.48; S, 6.77. Found: C, 55.67; H, 4.30; N, 8.79; Cl, 7.47; S, 6.56.

EXAMPLE 62

8-chlorodibenz[b,f][1,4]oxazepine-10(11H)-carboxylic acid,
2-[5-(2-pyridyl)thienylcarbonyl]hydrazide
(62)

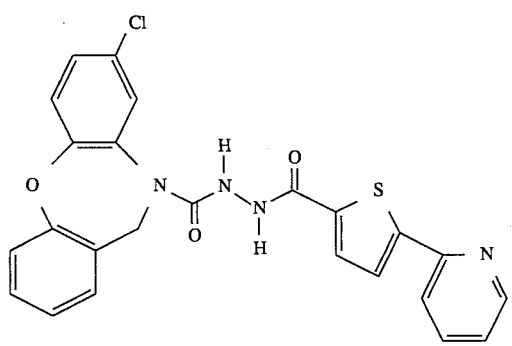

8-chlorodibenz[b,f][1,4]oxazepine-10(11H)-carboxylic acid, 2-[5-(2-pyridyl)thienylcarbonyl]hydrazide (62) was prepared in the manner described in Example 7 on a 10 mmol scale from 8-chlorodibenz[b,f][1,4]oxazepine-10(11H)-carboxylic acid, hydrazide (1), prepared as described above in Example 1, and 5-(2-pyridyl)thiophene-2-carboxylic acid. The yield of product was 1.33 g (28%). Analysis calculated for $C_{24}H_{17}N_4O_3SCl$ (M.W. 476.95): C, 60.44; H, 3.59; N, 11.75; Cl, 7.43; S, 6.72. Found: C, 60.18; H, 3.66; N, 11.69; Cl, 7.79; S, 6.63.

EXAMPLE 63

8-chlorodibenz[b,f][1,4]oxazepine-10(11H)-carboxylic acid,
2-[2,2-difluoro-3R-hydroxy-1-oxo-3-(2-pyridinyl)-propyl]hydrazide, monohydrochloride (Left Compound); and 8-chlorodibenz[b,f][1,4]oxazepine-10(11H)-carboxylic acid,
2-[2,2-difluoro-3S-hydroy-1-oxo-3-(2-pyridinyl)-propyl]hydrazide, acetate, monohydrochloride (Right Compound)

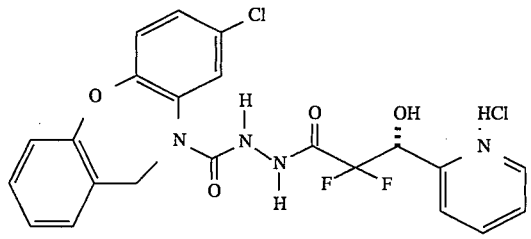

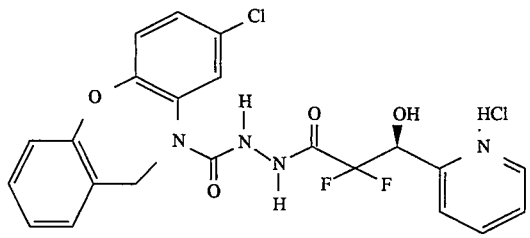

The isomers contained in the isomeric mixture described in Example 11 were separated by chiral column chromatography on a commercially-available Chiralcel AD column. The rotations are $[\alpha]_{589} = -8.70 \pm 2.80$ (compound shown above on the left) and $+18.9 \pm 2.80$ (compound shown above on the right), respectively. By chiral analytical HPLC, the products are single isomers with retention times of 16.44 minutes (compound shown above on the left) and 26.0 minutes (compound shown above on the right), respectively. The hydrochloride is prepared in the same manner as is described in Example 11A.

EXAMPLE 64

8-chlorodibenz[b,f][1,4]oxazepine-10(11H)-carboxylic acid,
2-[(1-oxo-3-(4-pyridinyl)propyl]hydrazide, N-oxide

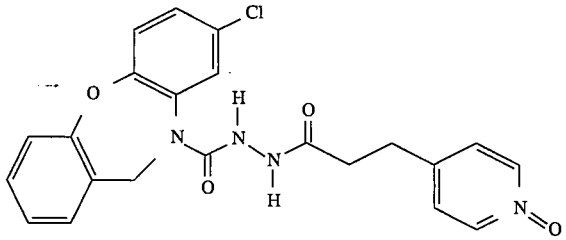

In this example, the product of Example 44 was converted into its corresponding N-oxide derivative.

(1) Conversion of the Product of Example 44 into its Free Base 50 g of the product of Example 44 (110 mmol) was dissolved in 2 L of deionized water. Neutralization of the hydrochloride was achieved by the dropwise addition of 110 mL of a solution of 1N NaOH (110 mmol) under constant stirring. This neutralization led, finally, to an aqueous suspension of the free base. The resulting white crystals were filtered, washed with 0.5 mL water, and dried overnight at 50° C. Yield: 44.4 g (95.5%).

(2) Oxidation of the Free Base of the Product of Example 44 into the Product of this Example 22 g (52 mmol) of the free base of the product of Example 44 was suspended in 2.5 L of $CH_2Cl_2$. To this suspension was added dropwise, over 30 minutes, a solution of 13.3 g of m-chloroperoxybenzoic acid (87 mmol) in 135 mL of $CH_2Cl_2$. During this addition, complete dissolution of the starting material was observed. Progression of the reaction was controlled by Thin Layer Chromatography (TLC) on silicagel eluted with $CH_2Cl_2$: $CH_3OH$:$NH_4OH$ 25% (v/v) (Product of Example 44: $R_f$ 0.58; Product of this example: $R_f$ 0.72).

Complete consumption of the starting material was achieved by stirring the reaction mixture overnight at room temperature. The organic phase was treated with 600 mL Of an aqueous solution of 3% $Na_2CO_3$ and washed successively with 600 mL of water. During this operation, the organic phase became turbid. It was dried by stirring with 60 g of $MgSO_4$. After filtration, the cake was washed with 2 L of a mixture of $CH_2Cl_2$:$CH_3OH$ (90:10, v/v).

This washing step was controlled by TLC to monitor desorption of reaction product trapped into the $MgSO_4$ cake. The pooled organic phases were evaporated to dryness to afford a residue. This residue was suspended under stirring in 150 mL of ethanol for 2 hours. The crystals were collected by filtration, washed with 10 mL of ethanol and dried overnight under reduced pressure at 50° C. Yield: 19.65 g (86%) of the product of this example.

(3) Recrystallization of the Product of this Example 37.45 g of crystals from Step (2) directly above (from a pool of two successive batches) dissolved in 2.4 L of methanol at 40° C. was treated under stirring for 15 minutes with 6 g of charcoal. After filtration on millipore, the resulting filtrate was concentrated under reduced pressure (bath temperature 50° C.), taken up with 500 mL of abs ethanol, and concentrated again under reduced pressure to a residual crystalline suspension of about 250 g. This suspension was left at room temperature under stirring for 2 hours to achieve the crystallization. The crystals were collected by filtration, washed with 20 mL of ethanol, and dried overnight under reduced pressure at 45° C. (mp 193.7° C.). Yield: 32.2 g (86%).

$^1$H-NMR (DMSO-$d_6$) δ (ppm): 8.9–9.5 (1H, s, —NH—C=O), 8.5–8.8 (1H, s, —NH—C=O), 8.07 (2H, d, =CH—N—O), 7.25 (2H, d, —CH=CH—N—O), 7.0–7.4 (7H, massive, aromatic protons), 4.8 (2H, s, —CH$_2$—N), 2.8 (2H, t, —CH$_2$—C=O), 2.3 (2H, t, —CH$_2$—CH$_2$—C=O).

Elemental analysis calculated for $C_{22}H_{19}N_4O_4Cl$ (Mol. Weight: 438.87): C, 60.21; H, 4.36; N, 12.77; Cl, 8.08. Found: C, 59.88; H, 4.26; N, 12.49; Cl, 8.27.

EXAMPLE 65

1H-imidazole-1-carbothioic acid, O-[2,2-difluoro-1-(2-pyridinyl)-3-ethoxy-3-oxopropyl]ester

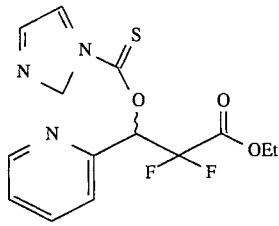

The 1.16 g (5 mmol) of ester described in Example 10 in 10 mL of ethylene dichloride is treated with 1.78 g (10 mmol) of thiocarbonyldiimidazole and 0.06 g (0.5 mmol) of dimethylaminopyridine. After 1 hour, the reaction mixture is applied to a column of silica gel for purification to yield 1.04 g (59%) of product. The product is used immediately in the following example.

EXAMPLE 66 ethyl α,α-difluoro-2-pyridinepropanoate

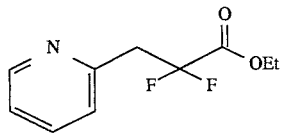

The product of Example 65 (0.51 g, 1.5 mmol) in 10 mL of toluene-DOM (4:1) was added dropwise to a refluxing 10 mn toluene solution of tri-n-butyltin hydride (0.88 g, 3.0 mmol). After 2 hours, the reaction mixture was filtered through a pad of silica gel which was washed with DCM and EtOAc. The product was in the EtOAc wash. The yield was 0.18 g (56%).

EXAMPLE 67

α,α-difluoro-2-pyridinepropanoic acid, hydrazide

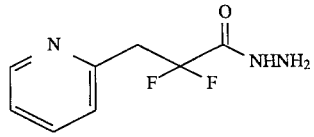

The product of Example 66 (0.18 g, 0.84 mmol) was dissolved in 5 mL of EtOH. To the solution was added $NH_2NH_2.H_2O$ (0.084 g, 1.7 mmol). The reaction was complete in 1 hour. The solvent was removed under vacuum. The structure was confirmed by $^1H$ NMR.

EXAMPLE 68

8-chlorodibenz[b,f][1,4]oxazepine-10(11H)-carboxylic acid, 2-[2,2-difluoro-1-oxo-3-(2-pyridinyl]propyl]hydrazide

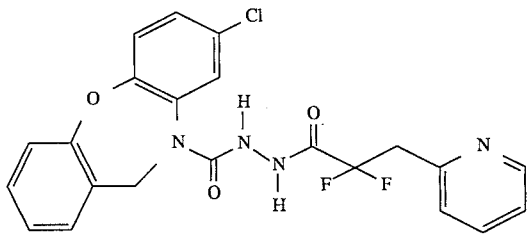

The product of Example 67 (0.31 g, 1.5 mmol) was dissolved in 5 mL of dimethylacetamide. To the stirring solution was added the product of Example 2 (0.45 g, 1.5 mmol) and triethylamine (0.42 mL, 3.0 mmol). After 20 hours of stirring at room temperature, the reaction was added to 25 mL of EtOAc and 25 mL of $H_2O$. The layers were separated. The organic phase was washed with 25 mL of $H_2O$ and 25 mL of brine. After drying and stripping the organic phase, the product was purified by flash chromatography to yield 51% of product. The hydrochloride was prepared in the same manner as is described in Example 11A.

Analysis calculated for $C_{22}H_{17}N_4O_3ClF_2.0.75$ HCl.0.5 $H_2O$ (M.W. 495.21): C, 53.36; H, 3.82; N, 11.31; Cl, 12.53. Found: C, 53.53; H, 3.47; N, 11.00; Cl, 12.80.

EXAMPLE 69

8-chlorodibenz[b,f][1,4]oxazepine-10(11H)-carboxylic acid, 2-[2,2-difluoro-3R-hydroxy-1-oxo-(4-pyrididyl)-propyl]hydrazide

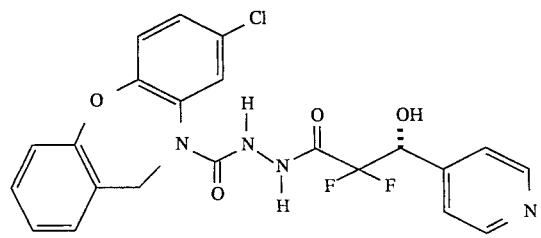

8-chlorodibenz[b,f][1,4]oxazepine-10(11H)-carboxylic acid, 2-[2,2-difluoro-3S-hydroxy-1-oxo-(4-pyridinyl)-propyl]hydrazide

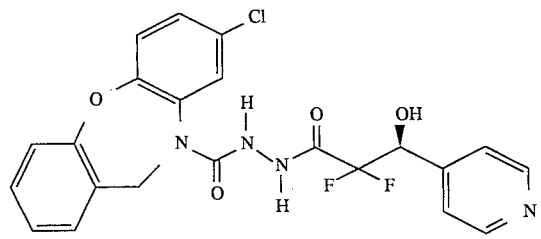

The isomers contained in the isomeric mixture described in example 51 are separated by chiral column chromatography on a commercially-available Chiralcel AD column.

EXAMPLE 70

8-chlorodibenz[b,f][1,4]oxazepine-10(11H)-carboxylic acid, 2-[2,2-difluoro-1-oxo-3-(4-pyridinyl)propyl]hydrazide

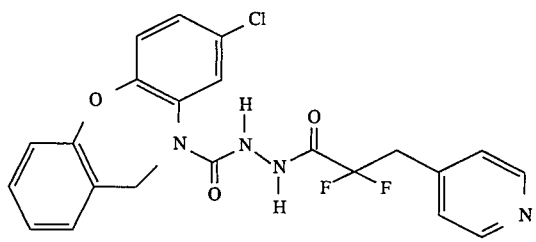

The product of this example is prepared in the same manner as the product of Example 68, with the exception that α,α-difluoro-4-pyridinepropanoic acid, hydrazide is employed in place of the product of Example 67.

The foregoing examples are provided to enable one skilled in the art to practice the present invention. These examples are merely illustrative, however, and should not be read as limiting the scope of the invention as it is claimed in the appended claims.

(7) Description of Assays (a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (19$9); and Witken et al., *J. Pharmacol. exp. Ther.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I below.

Charles River male albino mice, weighing 20 to 30 grams were used in this assay.

Thirty minutes after subcutaneous or intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, are presented in Table I below.

The standard initial screening dose of a test compound employed in this assay was 30 mpk per gram of body weight for both routes of administration. If this initial screening dose of the test compound produced analgesia in seven of ten mice, then the effect of additional doses of the test compound on the writhing response was evaluated, and then the $ED_{50}$ dose was generally calculated. (The slopes of the dose-response curves for all test compounds analyzed were compared as described by Tallarida and Murray, *Manual of Pharmacologic Calculations*, Page 11 (Springer Verlag, New York, 1981)).

All $ED_{50}$ doses calculated are also presented in Table I. As Table I shows, the rank order of potency of the more potent compounds of the present invention tested in the Writhing Assay was (referring to the particular example which describes the preparation of the compound): Example 13>Examples 9 and 44>Examples 6 and 6A>Example 11A. Thus, 8-chlorodibenz[b,f][1,4]oxazepine-10(11H)-carboxylic acid, 2-[3-[2-furanylmethyl)thio]-1-oxopropyl]hydrazide (13) (Example 13) was determined to be the most potent compound of the invention tested and, thus, is the most preferred compound of the present invention.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound antagonizes prostaglandin $E_2$.

Male albino guinea pigs weighing 200 to 500 grams were sacrificed by cervical dislocation.

The ileums were then quickly removed from the guinea pigs and placed in a modified Tyrode solution, a solution which is known to those of skill in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide.

Submaximal contractions of the ileum segments were then generated by injecting prostaglandin $E_2$ into the bath, and detected isotonically. Data for a control prostaglandin $E_2$ dose response curve plotting concentration of prostaglandin $E_2$ versus number of contractions generated was then obtained by experimentally adjusting the dose of the prostaglandin $E_2$ being injected into the tissue bath, in a manner known by those of skill in the art.

Solutions or suspensions containing an initial amount of a test compound in modified Tyrode solution ("test solutions/suspensions") were then separately substituted for the tissue bath. Each test solution/suspension was then kept in constant contact with the ileum tissue, except for brief periods to drain the bath in preparation for rinsing with fresh test solution/suspension. Different doses of prostaglandin $E_2$ were again injected into the test solutions/suspensions.

A second prostaglandin $E_2$ dose response curve was then generated for prostaglandin $E_2$ in the presence of a test compound.

A dose ratio of $EC_{50}$ dose values was then calculated from the results of each test in a manner known by those of skill in the art. A concentration of test compound was determined to be "active" if it produced a dose ratio significantly greater than that obtained in a series of blank treatments. Duplicate tests were conducted on each concentration of test compound.

If the initial concentration of a test compound was determined to be "active," then varying concentrations of the test compound were then assayed. As is shown in Table I below, all test compounds analyzed in this assay were determined to be "active" as prostaglandin $E_2$ antagonists at the initial concentration.

The $pA_2$ value (a statistical constant which is a common measure of expressing the potency of a particular drug as a competitive antagonist) was then calculated for each test compound by schild plot calculations, as described by H. O. Schild, "pA, A New Scale for the Measurement of Drug Antagonism," *Br. J. Pharmacol,* 2, 189 (1947), according to the following mathematical formula:

$$pA_2 = -\log[\text{Test Compound}]$$

to quantitate the effectiveness of the test compounds as prostaglandin $E_2$ antagonists. The higher the value calculated for $pA_2$, the more potent a particular compound is as a prostaglandin $E_2$ antagonist.

The results of this prostaglandin antagonism assay are also presented in Table I below. The compounds of the present invention which were tested in this assay, and for which results are presented in Table I, correspond to the particular examples specified in Table I.

The results in Table I show that all of the compounds of the present invention tested in this assay exhibit activity as prostaglandin $E_2$ antagonists. Some of these compounds, such as 8-chlorodibenz-[b,f][1,4]oxazepine-10(11H)-carboxylic acid, 2-[3-[(2-furanyl-methyl)thio]-1-oxopropyl]hydrazide (13), the synthesis of which is described above in Example 13, were surprisingly and unexpectedly found to be more than eighty times more effective as prostaglandin $E_2$ antagonists than prostaglandin $E_2$ antagonists reported in the literature.

TABLE I

| | | Data Generated from the Assays | | |
|---|---|---|---|---|
| | EXAMPLE NUMBER | PBO WRITING ASSAY ($ED_{50}$ (mpk)) | | PGE ANTAGONISM IN GUINEA PIG ILEUM |
| —$(X)_q$—$(Y)_r$—$(CH_2)_m$—Ar | NUMBER | I.G. | S.C. | ($pA_2$) |
| —$(CH_2)_3$-2-thienyl | 9 | Active (6.8) | Active | Active (7.6) |
| —$(CH_2)_2$NH—$CH_2$-2-thienyl.HCl | 18 | Active (6.6) | Active (1.9) | Active (7.0) |
| —$CH_2OCH_2$-2-thienyl | 21 | Active | Active | Active (6.6) |
| —$(CH_2)_2$-2-pyridyl | 6 | Active (8.6) | Active | Active (5.6) |
| —$(CH_2)_2$NH-2-$CH_2$-2-furanyl | 25 | Active (10.9) | Active (1.9) | Active (5.7) |
| —$CF_2$CHOH-2-thienyl | 27 | Active | Active | Active (5.9) |
| —CH=CH-3-pyridyl | 7 | Active | Active | Not Yet Tested |
| —$(CH_2)_2$-3-pyridyl.HCl | 8 | Active | Active | Not Yet Tested |
| —CH=CH-4-pyridyl | 45 | * | * | Not Yet Tested |
| —$(CH_2)_2$-2-pyridyl-N-oxide | 14 | * | * | Not Yet Tested |
| -4-pyridyl.HCl | 34 | * | * | Not Yet Tested |
| -3-pyridyl.HCl | 35 | * | * | Not Yet Tested |
| -2-pyridyl-5-butyl.HCl | 37 | * | * | Not Yet Tested |
| —CH=CH-2-pyridyl | 38 | * | * | Not Yet Tested |
| —$CH_2$-2-pyridyl.HCl | 39 | * | * | Not Yet Tested |
| —$CH_2$-3-pyridyl.HCl | 40 | * | Active | Not Yet Tested |
| —$CH_2$-4-pyridyl.HCl | 41 | * | * | Not Yet Tested |
| —$(CH_2)_2$-4-pyridyl.HCl | 44 | Active (6.8) | Active (6.3) | Active (6.5) |
| -2-pyridyl.HCl | 36 | * | * | Not Yet Tested |
| —$CF_2$CHOH-2-pyridyl | 11 | Active | Active | Active (7.6) |
| —$CF_2$CHOH-2-pyridyl.HCl | 11A | Active (9.1) | Active (4.1) | Active (7.3) |
| —$(CH_2)_2$S—$CH_2$-2-furanyl | 13 | Active (0.9) | * | Active (8.5) |
| —$(CH_2)_3$-2-pyridyl.HCl | 47 | Active | Active | Not Yet Tested |
| —$(CH_2)_3$-4-pyridyl.HCl | 49 | Active | Active | Not Yet Tested |

TABLE I-continued

Data Generated from the Assays

| —(X)$_q$—(Y)$_r$—(CH$_2$)$_m$—Ar | EXAMPLE NUMBER | PBO WRITHING ASSAY (ED$_{50}$ (mpk)) | | PGE ANTAGONISM IN GUINEA PIG ILEUM (pA$_2$) |
|---|---|---|---|---|
| | | I.G. | S.C. | |
| —CH$_2$-e-CH=CH-3-thienyl | 30 | * | * | Not Yet Tested |
| —CH$_2$-z-CH=CH-3-thienyl | 31 | * | * | Not Yet Tested |
| —(CH$_2$)$_3$-3-thienyl | 33 | Active | * | Not Yet Tested |
| —(CH$_2$)$_2$SOCH$_2$-2-furanyl | 60 | * | * | Active (6.2) |
| —(CH$_2$)$_2$SO$_2$CH$_2$-2-furanyl | 61 | * | * | Active (6.6) |
| -2-thienyl-4-(2-pyridyl) | 62 | Active | Active | Not Yet Tested |
| —(CH$_2$)$_2$SCH$_2$-2-pyridyl.HCl | 54 | Active | * | Active (6.8) |
| —CF$_2$CHOH-4-pyridyl.HCl | 51 | Active | * | Not Yet Tested |
| —(CH$_2$)$_4$-2-thienyl | 59 | * | * | Not Yet Tested |
| —(CH$_2$)$_2$SCH$_2$-2-thienyl | 57 | * | * | Not Yet Tested |
| —(CH$_2$)$_2$-4-pyridyl-N-oxide | 64 | Active | Not Yet Tested | Not Yet Tested |
| —CF$_2$CH$_2$-2-pyridyl | 68 | Active (9.7) | Not Yet Tested | Not Yet Tested |

\* = Indicates that, in accordance with the particular conditions set forth above for the Wrathing Assay, and under the test criteria employed for that assay, after the administration of an initial screening dosage of 30 mg per kilogram of the compound, the number of writhes elicited by a mouse injected with PBQ was not equal to, or less than, one-half the median number of writhes recorded for the saline-treated control group of mice that day.

While the present invention has been described herein with some specificity, and with reference to certain preferred embodiments thereof, those of ordinary skill in the art will recognize variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated to induce analgesia, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A method for treating osteoporosis in an animal comprising administering to said animal a therapeutically-effective amount of a compound having the structure:

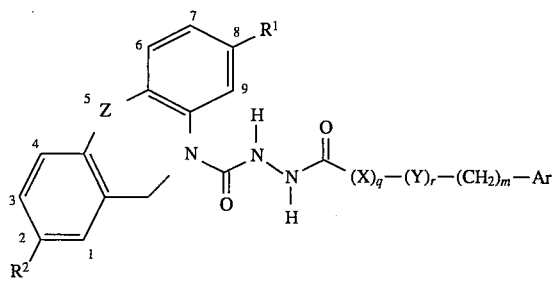

or a pharmaceutically-acceptable salt thereof, wherein:

$R^1$ is: hydrogen, halogen or —CF$_3$;

$R^2$ is: hydrogen, halogen, —OH or —OCH$_3$;

Z is: oxygen, sulfur,

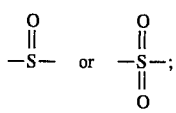

X is: —CH=CH—, —CF$_2$—, —CHF—, —(CH$_2$)$_n$— or —(CH$_2$)$_p$—CH=CH—;

Y is:

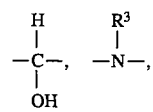

sulfur,

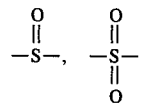

or oxygen;

q is: 0 or 1;

r is: 0 or 1, provided that r is not 0 when:
   (1) X is —CH=CH—, —(CH$_2$)$_n$— or —(CH$_2$)$_p$—CH=CH—, q is 1 and Ar is imidazolyl or phenyl,
   (2) X is —(CH$_2$)$_n$—, q is 1 and Ar is phenyl or alkyl-substituted phenyl, or
   (3) q is 0, m is 1, 2, 3, 4, 5 or 6, and Ar is imidazolyl, phenyl or alkyl-substituted phenyl;

m is: an integer of from 0 to 6, provided that m is not 0 when X is —(CH$_2$)$_n$—, q is 1, Y is oxygen, sulfur,

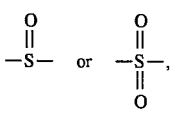

r is 1, and Ar is phenyl or alkyl-substituted phenyl;

n is: an integer of from 1 to 6;

p is: an integer of from 1 to 6;

R³ is: hydrogen or t-butyloxycarbonyl; and

Ar is: aryl, alkyl-substituted aryl or aryl-substituted aryl.

2. The method of claim 1 wherein the compound is selected from the group consisting of:

8-chlorodibenz[b,f][1,4]oxazepine-10(11H)-carboxylic acid, 2-[1-oxo-3-(2-pyridinyl)propyl]-hydrazide;

8-chlorodibenz[b,f][1,4]oxazepine-10(11H)-carboxylic acid, 2-[1-oxo-3-(2-pyridinyl)propyl]hydrazide, monohydrochloride;

8-chlorodibenz[b,f][1,4]oxazepine-10(11H)-carboxylic acid, 2-[1-oxo-4-(2-thienyl)butyl]-hydrazide;

8-chlorodibenz[b,f][1,4]oxazepine-10(11H)-carboxylic acid, 2-[2,2-difluoro-3-hydroxy-1-oxo-3-(2-pyridinyl)-propyl]hydrazide;

8-chlorodibenz[b,f][1,4]oxazepine-10(11H)-carboxylic acid, 2-[2,2-difluoro-3-hydroxy-1-oxo-3-(2-pyridinyl)-propyl]hydrazide, monohydrochloride;

8-chlorodibenz[b,f][1,4]oxazepine-10(11H)-carboxylic acid, 2-[3-[(2-furanylmethyl)thio]-1-oxopropyl]hydrazide;

8-chlorodibenz[b,f][1,4]oxazepine-10(11H)-carboxylic acid, 2-[1-oxo-3-(2-thienylmethyl)-amino]propylhydrazide, monohydrochloride;

8-chlorodibenz[b,f][1,4]oxazepine-10(11H)-carboxylic acid, 2-[(2-thienylmethoxy)acetyl]-hydrazide;

8-chlorodibenz[b,f][1,4]oxazepine-10(11H)-carboxylic acid, 2-[3-[(2-furanylmethyl)amino]-1-oxopropyl]hydrazide;

8-chlorodibenz[b,f][1,4]oxazepine-10(11H)-carboxylic acid, 2-[2,2-difluoro-3-hydroxyl-1-oxo-3-(2thienyl)-propyl]hydrazide;

8-chlorodibenz[b,f][1,4]oxazepine-10(11H)-carboxylic acid, 2-[1-oxo-3-(4-pyridinyl)propyl]-hydrazide, monohydrochloride;

8-chlorodibenz[b,f][1,4]oxazepine-10(11H)-carboxylic acid, 2-[3-[2-(pyridylmethyl)thio]-1-oxopropyl]hydrazide;

8-chlorodibenz[b,f][1,4]oxazepine-10(11H)-carboxylic acid, 2-[3-[(2-furanylmethyl)sulfinyl]-1-oxopropyl]hydrazide;

8-chlorodibenz[b,f][1,4]oxazepine-10(11H)-carboxylic acid, 2-[3-[(2-furanylmethyl)sulfonyl]-1-oxopropyl] hydrazide;

8-chlorodibenz[b,f][1,4]oxazepine-10(11H)-carboxylic acid, 2-[2,2-difluoro-3R-hydroxy-1-oxo-3-(2-pyridinyl)propyl]hydrazide, monohydrochloride;

8-chlorodibenz[b,f][1,4]oxazepine-10(11H)-carboxylic acid, 2-[2,2-difluoro-3S-hydroxy-1-oxo-3-(2-pyridinyl)propyl]hydrazide, acetate, monohydrochloride; and 8-chlorodibenz[b,f][1,4]oxazepine-10(11H)-carboxylic acid, 2-[2,2-difluoro-1-oxo-3-(2-pyridinyl)propyl]hydrazide.

3. A method for treating ischemia in an animal comprising administering to said animal a therapeutically-effective amount of a compound having the structure:

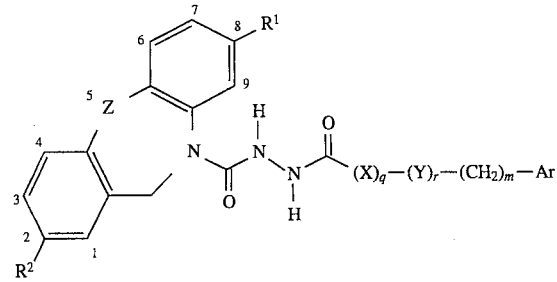

or a pharmaceutically-acceptable salt thereof, wherein:

R¹ is: hydrogen, halogen or —CF₃;

R² is: hydrogen, halogen, —OH or —OCH₃;

Z is: oxygen, sulfur,

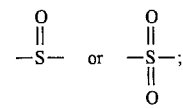

X is: —CH=CH—, —CF₂—, —CHF—, —(CH₂)$_n$— or —(CH₂)$_p$—CH=CH—;

Y is:

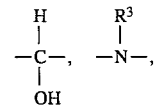

sulfur,

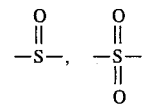

or oxygen;

q is: 0 or 1;

r is: 0 or 1, provided that r is not 0 when:
(1) X is —CH=CH—, —(CH₂)$_n$— or —(CH₂)$_p$—CH=CH—, q is 1 and Ar is imidazolyl or phenyl,
(2) X is —(CH₂)$_n$—, q is 1 and Ar is phenyl or alkyl-substituted phenyl, or
(3) q is 0, m is 1, 2, 3, 4, 5 or 6, and Ar is imidazolyl, phenyl or alkyl-substituted phenyl;

m is: an integer of from 0 to 6, provided that m is not 0 when X is —(CH₂)$_n$—, q is 1, Y is oxygen, sulfur,

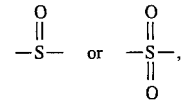

r is 1, and Ar is phenyl or alkyl-substituted phenyl;

n is: an integer of from 1 to 6;

p is: an integer of from 1 to 6;

R³ is: hydrogen or t-butyloxycarbonyl; and

Ar is: aryl, alkyl-substituted aryl or aryl-substituted aryl.

4. The method of claim 3 wherein the compound is selected from the group consisting of:

8-chlorodibenz [b,f][1,4]oxazepine-10(11H) -carboxylic acid, 2-[1-oxo-3-(2-pyridinyl)propyl]-hydrazide;

8-chlorodibenz[b,f][1,4]oxazepine-10(11H)-carboxylic acid, 2-[1-oxo-3-(2-pyridinyl)propyl]hydrazide, monohydrochloride;

8-chlorodibenz[b,f][1,4]oxazepine-10(11H)-carboxylic acid, 2-[1-oxo-4-(2-thienyl)butyl]-hydrazide;

8-chlorodibenz[b,f][1,4]oxazepine-10(11H)-carboxylic acid, 2-[2,2-difluoro-3-hydroxy-1-oxo-3-(2-pyridinyl)propyl]hydrazide;

8-chlorodibenz[b,f][1,4]oxazepine-10(11H)-carboxylic acid, 2-[2,2-difluoro-3-hydroxy-1-oxo-3-(2-pyridinyl)propyl]hydrazide, monohydrochloride;

8-chlorodibenz[b,f][1,4]oxazepine-10(11H)-carboxylic acid, 2-[3-[(2-furanylmethyl)thio]-1-oxopropyl]hydrazide;

8-chlorodibenz[b,f][1,4]oxazepine-10(11H)-carboxylic acid, 2-[1-oxo-3-(2-thienylmethyl)-amino]propylhydrazide, monohydrochloride;

8-chlorodibenz[b,f][1,4]oxazepine-10 (11H)-carboxylic acid, 2-[(2-thienylmethoxy)acetyl]-hydrazide;

8-chlorodibenz[b,f][1,4]oxazepine-10(11H)-carboxylic acid, 2-[3-[(2-furanylmethyl)amino]-1-oxopropyl]hydrazide;

8-chlorodibenz[b,f][1,4]oxazepine-10(11H)-carboxylic acid, 2-[2,2-difluoro-3-hydroxyl-1-oxo-3-(2-thienyl)propyl]hydrazide;

8-chlorodibenz[b,f][1,4]oxazepine-10(11H)-carboxylic acid, 2-[1-oxo-3-(4-pyridinyl)propyl]-hydrazide, monohydrochloride;

8-chlorodibenz[b,f][1,4]oxazepine-10(11H)-carboxylic acid, 2-[3-[2-(pyridylmethyl)thio]-1-oxopropyl]hydrazide;

8-chlorodibenz[b,f][1,4]oxazepine-10(11H)-carboxylic acid, 2-[3-[(2-furanylmethyl)sulfinyl]-1-oxopropyl]hydrazide;

8-chlorodibenz[b,f][1,4]oxazepine-10(11H)-carboxylic acid, 2-[3-[(2-furanylmethyl)sulfonyl]-1-oxopropyl] hydrazide;

8-chlorodibenz[b,f][1,4]oxazepine-10(11H)-carboxylic acid, 2-[2,2-difluoro-3R-hydroxy-1-oxo-3-(2-pyridinyl)propyl]hydrazide, monohydrochloride;

8-chlorodibenz[b,f][1,4]oxazepine-10(11H)-carboxylic acid, 2-[2,2-difluoro-3S-hydroxy-1-oxo-3-(2-pyridinyl)propyl]hydrazide, acetate, monohydrochloride; and 8-chlorodibenz[b,f][1,4]oxazepine-10(11H)-carboxylic acid, 2-[2,2-difluoro-1-oxo-3-(2-pyridinyl)propyl]hydrazide.

* * * * *

UNITED STATES PATENT AND TRADEMARK OFFICE
CERTIFICATE OF CORRECTION

PATENT NO. : 5,576,315

DATED : November 19, 1996

INVENTOR(S) : E. ANN HALLINAN ET AL.

Page 1 of 6

It is certified that error appears in the above-identified patent and that said Letters Patent is hereby corrected as shown below:

On the title page, item
[56] REFERENCES CITED

Other Publications, Under "A. Bennett, et al.", "Soduim" should read --Sodium--.

COLUMN 1

Line 9, "37 CFU § 1.60" should read --37 C.F.R. § 1.60--.
Line 53, "dibenzodiazepinecar-" should read --dibenzodiazepine-car- --

COLUMN 2

Line 27, "European" should read --European--.

COLUMN 4

Line 57, "compounds" should read --Compounds--.

COLUMN 6

Line 57, "t-buryloxy-" should read --t-butyloxy--.

UNITED STATES PATENT AND TRADEMARK OFFICE
CERTIFICATE OF CORRECTION

PATENT NO. : 5,576,315

DATED : November 19, 1996

INVENTOR(S) : E. ANN HALLINAN ET AL.

It is certified that error appears in the above-identified patent and that said Letters Patent is hereby corrected as shown below:

COLUMN 7

Line 42, "lare," should read --lar,--.
    Line 43, "ingection" should read --injection--.

COLUMN 9

Line 22, "palmirate," should read --palmitate,--.

COLUMN 18

Line 17, "Pharmaceutically-acceptable" should read --pharmaceutically-acceptable--.

COLUMN 19

Line 14, "a" should read --as--.

COLUMN 21

Line 2, "ingectable" should read --injectable--.
    Line 29, "Polylactide-polyglycolide." should read --polylactide-polyglycolide.--.
    Line 45, "ingec-" should read --injec- --.

UNITED STATES PATENT AND TRADEMARK OFFICE
CERTIFICATE OF CORRECTION

PATENT NO. : 5,576,315

DATED : November 19, 1996

INVENTOR(S) : E. ANN HALLINAN ET AL.

It is certified that error appears in the above-identified patent and that said Letters Patent is hereby corrected as shown below:

COLUMN 22

Line 24, "Mannhelm" should read --Mannheim--.
    Line 37, "-10(11M)-" should read -- -10(11H)- --.
    Line 58, "1:1 ethermethylene    should read
      --1:1 ether-methylene--.

COLUMN 25

Line 63, "hererogenous" should read --heterogenous--.

COLUMN 33

Line 3, "(2-furanylmetyl)" should read
      --(2-furanylmethyl)--
    Line 15, "furrural" should read --furfinal--.

COLUMN 40

Line 41, "95:5)" should read --95:5:0.5)--.

COLUMN 44

Line 54, "propanoane" should read --propanoate--.

UNITED STATES PATENT AND TRADEMARK OFFICE
CERTIFICATE OF CORRECTION

PATENT NO. : 5,576,315

DATED : November 19, 1996

INVENTOR(S) : E. ANN HALLINAN ET AL.

It is certified that error appears in the above-identified patent and that said Letters Patent is hereby corrected as shown below:

COLUMN 46

Line 39, "Toga" should read --To a--.

COLUMN 49

Line 11, "hydrazide 49)." should read --hydrazide (49).--.

COLUMN 55

Line 11, "-hydroy-" should read -- -hydroxy- --.

COLUMN 56

Line 26, "Of" should read --of--.

COLUMN 57

Line 21, "dimethylaminopyridine." should read --dimethyl-aminopyridine.--.
    Line 66, "solvent-was" should read --solvent was--.

UNITED STATES PATENT AND TRADEMARK OFFICE
CERTIFICATE OF CORRECTION

PATENT NO. : 5,576,315

DATED : November 19, 1996

INVENTOR(S): E. ANN HALLINAN ET AL.

It is certified that error appears in the above-identified patent and that said Letters Patent is hereby corrected as shown below:

COLUMN 59

Line 2, "example 51" should read --Example 51--.
    Line 43, "(19$9);" should read --(1959);--.

COLUMN 62

Line 16, "quantirate" should read --quantitate--.
    Table 1, -CH-CH-4-pyridyl" should read
      -- -CH=CH-4-pyridyl--.

COLUMN 63

Table 1, "Wrathing" should read --Writhing--.

UNITED STATES PATENT AND TRADEMARK OFFICE
CERTIFICATE OF CORRECTION

PATENT NO.  : 5,576,315
DATED       : November 19, 1996
INVENTOR(S) : E. ANN HALLINAN ET AL.

It is certified that error appears in the above-identified patent and that said Letters Patent is hereby corrected as shown below:

<u>COLUMN 65</u>

Line 38 "-(2thienyl)-" should read -- -(2-thienyl)- --.

Signed and Sealed this

Twenty-seventh Day of May, 1997

BRUCE LEHMAN

*Attest:*

*Attesting Officer*     *Commissioner of Patents and Trademarks*